United States Patent
Chiang et al.

(10) Patent No.: US 12,281,358 B2
(45) Date of Patent: *Apr. 22, 2025

(54) HONEYCOMB TUBE

(71) Applicant: Cepheid, Sunnyvale, CA (US)

(72) Inventors: Yuh-Min Chiang, Sunnyvale, CA (US);
Doug Dority, Santa Cruz, CA (US);
Dustin Dickens, Santa Clara, CA (US);
Jennifer Glass, San Jose, CA (US);
Reuel Van Atta, Palo Alto, CA (US)

(73) Assignee: Cepheid, Sunnyvale, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/350,916

(22) Filed: Aug. 7, 2023

(65) Prior Publication Data

US 2024/0076737 A1     Mar. 7, 2024

Related U.S. Application Data

(60) Continuation of application No. 16/992,392, filed on Aug. 13, 2020, now Pat. No. 11,739,383, which is a
(Continued)

(51) Int. Cl.
*B01L 3/00* (2006.01)
*C12Q 1/6876* (2018.01)
*B01L 7/00* (2006.01)

(52) U.S. Cl.
CPC ............ *C12Q 1/6876* (2013.01); *B01L 3/502* (2013.01); *B01L 3/5027* (2013.01);
(Continued)

(58) Field of Classification Search
None
See application file for complete search history.

(56) References Cited

U.S. PATENT DOCUMENTS

| 4,683,195 A | 7/1987 | Mullis et al. |
| 4,683,202 A | 7/1987 | Mullis |

(Continued)

FOREIGN PATENT DOCUMENTS

| CN | 1942590 | 4/2007 |
| CN | 101680013 | 3/2010 |

(Continued)

OTHER PUBLICATIONS

Bonants et al., "Quantitative multiplex detection of (plant) pathogens, including Phytophthora species, based on PRI-lock probe technology and the OpenArray platform," PowerPoint Presentation, Phytophthora, Pythium Workshop ICPP, Aug. 2008, Wageningen UR, 22 pages.

(Continued)

*Primary Examiner* — Brian R Gordon
(74) *Attorney, Agent, or Firm* — Potomac Law Group, PLLC; Reza Mollaaghababa; Michael J. Bastian

(57) ABSTRACT

A honeycomb tube with a planar frame defining a fluidic path between a first planar surface and a second planar surface. A fluidic interface is located at one end of the planar frame. The fluidic interface has a fluidic inlet and fluidic outlet. The fluidic path further includes a well chamber having an well-substrate with a plurality of wells. The well chamber is arranged in the planar frame between the first or second surface and the well-substrate.

25 Claims, 29 Drawing Sheets

Specification includes a Sequence Listing.

Related U.S. Application Data continuation of application No. 16/230,458, filed on Dec. 21, 2018, now Pat. No. 10,767,226, which is a division of application No. 14/431,259, filed as application No. PCT/US2013/062042 on Sep. 26, 2013, now Pat. No. 10,190,165, which is a continuation of application No. 13/843,739, filed on Mar. 15, 2013, now Pat. No. 9,914,968.

(60) Provisional application No. 61/706,115, filed on Sep. 26, 2012.

(52) U.S. Cl.
CPC ............ *B01L 3/50851* (2013.01); *B01L 7/52* (2013.01); *B01L 2200/0642* (2013.01); *B01L 2200/0673* (2013.01); *B01L 2300/0636* (2013.01); *B01L 2300/0819* (2013.01); *B01L 2400/0406* (2013.01); *B01L 2400/0487* (2013.01)

(56) References Cited

U.S. PATENT DOCUMENTS

| | | | |
|---|---|---|---|
| 4,800,159 | A | 1/1989 | Mullis et al. |
| 4,965,188 | A | 10/1990 | Mullis et al. |
| 4,988,617 | A | 1/1991 | Landegren et al. |
| 5,168,038 | A | 12/1992 | Tecott et al. |
| 5,210,015 | A | 5/1993 | Gelfand et al. |
| 5,273,718 | A | 12/1993 | Skold |
| 5,399,491 | A | 5/1995 | Kacian et al. |
| 5,427,930 | A | 6/1995 | Birkenmeyer et al. |
| 5,648,211 | A | 7/1997 | Fraiser et al. |
| 5,712,124 | A | 1/1998 | Walker |
| 5,854,033 | A | 12/1998 | Lizardi |
| 5,925,517 | A | 7/1999 | Tyagi et al. |
| 6,174,670 | B1 | 1/2001 | Wittwer et al. |
| 6,403,037 | B1* | 6/2002 | Chang ...................... B01L 7/52 422/68.1 |
| 6,569,627 | B2 | 5/2003 | Wittwer et al. |
| 6,716,629 | B2 | 4/2004 | Hess et al. |
| 6,818,185 | B1 | 11/2004 | Petersen et al. |
| 7,387,898 | B1 | 6/2008 | Gordon |
| 8,043,580 | B2 | 10/2011 | Nishigaya et al. |
| 8,048,386 | B2 | 11/2011 | Dority et al. |
| 8,119,352 | B2 | 2/2012 | Kozma et al. |
| 8,187,557 | B2 | 5/2012 | Van Atta et al. |
| 8,268,978 | B2 | 9/2012 | Mullah et al. |
| 8,394,324 | B2 | 3/2013 | Bousse et al. |
| 8,968,684 | B2 | 3/2015 | Lian |
| 9,914,968 | B2 | 3/2018 | Chiang et al. |
| 10,767,226 | B2 | 9/2020 | Chiang et al. |
| 2002/0121529 | A1* | 9/2002 | Hoummady ......... B01J 19/0046 222/113 |
| 2006/0263242 | A1 | 11/2006 | Yang |
| 2007/0003443 | A1 | 1/2007 | Sandell |
| 2007/0264705 | A1 | 11/2007 | Dodgson |
| 2008/0038737 | A1 | 2/2008 | Smith et al. |
| 2008/0108122 | A1 | 5/2008 | Paul |
| 2008/0202927 | A1* | 8/2008 | Kayyem ................. B01L 9/527 204/403.01 |
| 2009/0054266 | A1 | 2/2009 | Hasan et al. |
| 2009/0093374 | A1 | 4/2009 | Suh |
| 2010/0173310 | A1 | 7/2010 | Bousse et al. |
| 2010/0252128 | A1 | 10/2010 | Gong et al. |
| 2011/0143964 | A1 | 6/2011 | Zhou et al. |
| 2013/0004967 | A1 | 1/2013 | Halverson et al. |
| 2013/0052649 | A1* | 2/2013 | Lee ........................ B01L 3/5085 435/6.12 |
| 2013/0280725 | A1* | 10/2013 | Ismagilov ............. B01L 3/5027 435/6.12 |
| 2014/0087958 | A1 | 3/2014 | Chiang et al. |
| 2014/0295546 | A1 | 10/2014 | Adamson |
| 2016/0339427 | A1* | 11/2016 | Wiktor ................ B01J 19/0046 |
| 2017/0067091 | A1* | 3/2017 | Lin ....................... B01L 3/5027 |
| 2018/0126381 | A1* | 5/2018 | Huff ................. G01N 27/44721 |
| 2020/0270674 | A1* | 8/2020 | Hirase ..................... C12Q 1/686 |
| 2022/0106648 | A1* | 4/2022 | Hirase ..................... B01L 3/502 |

FOREIGN PATENT DOCUMENTS

| | | |
|---|---|---|
| JP | H04-262799 A2 | 9/1992 |
| JP | U3126208 | 9/2006 |
| JP | 2010271304 A | 12/2010 |
| JP | 2011506998 A | 3/2011 |
| WO | 2005-080606 A1 | 9/2005 |
| WO | 2005-120459 A2 | 12/2005 |
| WO | 2007043619 A1 | 4/2007 |
| WO | 2007-055887 A1 | 5/2007 |
| WO | 2012-049066 A2 | 4/2012 |
| WO | 2006-092569 A1 | 9/2016 |

OTHER PUBLICATIONS

Dixon et al., "Nanoliter high-throughput RT-qPCR: a statistical analysis and assessment," *Biotechniques*, 2009, vol. 46, No. 6, pp. ii-viii.

"The First True High-Density Next Generation Real-Time PCR System," Wafergen Biosystems, http:-- ewarga4.ukm.my-ewarga-pdf-052011-24-85.pdf, © 2010 8 pages.

Focke et al., "Centrifugal microfluidic system for primary amplification and secondary real-time PCR," Lab Chip, 2010, vol. 10, pp. 3210-3212.

Freeman et al., "Quantitative RT-PCR: pitfalls and potential," 1999, *Biotechniques*, vol. 26, No. 1, pp. 112-125.

Hashimoto et al., "Instrumentation of a PLC-Regulated Temperature Cycler with a PID Control Unit and Its Use for Miniaturized PCR Systems with Reduced Volumes of Aqueous Sample Droplets Isolated in Oil Phase in a Microwell," Analytical Sciences, Dec. 2011, vol. 27, pp. 1191-1196.

Hatch et al., "Multilayer High-Density 3D Nanowell Arrays for Digital Biology", 15th International Conference on Miniaturized Systems for Chemistry and Life Sciences, Seattle, Washington, USA, Oct. 2-6, 2011, pp. 269-271.

"Increasing speed while decreasing cost: PCR in nanoliter volumes," SciFLEXARRAYER Application Note No. 08004, Feb. 2008, http:--www.scienion.com-fileadmin-user_upload-pdf-sciApplication_Note_08004.pdf, 1 page.

Jackman et al., "Fabricating large arrays of microwells with arbitrary dimensions and filling them using discontinuous dewetting", *Analytical Chemistry*, 1998, vol. 70 no. 11, pp. 2280-2287.

Karnakis, "Laser Microdrilling in Industrial Applications," PowerPoint Presentation, Oct. 2004, www.designforlasermanufacture.com-assets-OLmicrodrill.pdf, 40 pages.

Leamon et al., "A massively parallel PicoTiterPlate based platform for discrete picoliter-scale polymerase chain reactions," *Electrophoresis*, 2003, vol. 24, pp. 3769-3777.

Liu et al., "Self-Contained, Fully Integrated Biochip for Sample Preparation, Polymerase Chain Reaction Amplification, and DNA Microarray Detection", *Analytical Chemistry*, 2004, vol. 76, No. 7, pp. 1824-1831.

Matsubara et al., "On-Chip Nanoliter-Volume Multiplex TaqMan Polymerase Chain Reaction from a Single Copy Based on Counting Fluorescence Released Microchambers," *Analytical Chemistry*, 2004, vol. 76, No. 21, pp. 6434-6439.

Men et al., "Digital Polymerase Chain Reaction in an Array of Femtoliter Polydimethylsiloxane Microreactors," *Analytical Chemistry*, 2012, vol. 84, pp. 4262-4266, with supporting information.

Minot et al., "Fiber Optic Interrogated (FOI) Microwell Biochips," INCOM Technical Bulletin No. 040225, http:--minotecheng.com-MicroWell_Technical_Bulletin_022504.pdf, 5 pages.

Nagi et al., "Development of a microchamber array for picoliter PCT," Analytical Chemistry, 2001, vol. 73, pp. 1043-1047.

Schillinger et al., "An isogeometric design-through-analysis methodology based on adaptive hierarchical refinement of NURBS, immersed boundary methods, and T-spline CAD surfaces," *Com-

(56) References Cited

OTHER PUBLICATIONS

*puter Methods in Applied Mechanics and Engineering*, submitted Jan. 22, 2012, published Dec. 2012, vol. 249-252, pp. 116-150.

Shen et al., "Nanoliter Multiplex PCR Arrays on a SlipChip," *Analytical Chemistry*, 2010, vol. 82, No. 11, pp. 4606-4612.

Slinger et al., "Respiratory Syncytial Virus (RSV) Detection in Clinical Specimens using a Nanoliter Real-time PCR Respiratory Pathogen Panel," Poster presented at the Pharyngitis American Society for Microbiology 109th General Meeting, May 2009, Philadelphia, Pennsylvania.

Squires et al., "Microfluidics: Fluid physics at the nanoliter scale," *Reviews of Modern Physics*, 2005, col. 77, pp. 977-1026.

Trung et al., "Accurate and reliable multi chamber PCT chip with sample loading and primer mixing using vaccum jackets for n x m quantitative analysis", 14th International Conference on Miniaturized System for Chemistry and Life Sciences, Groningen, The Netherlands, 2010, pp. 1775-1777.

Wang et al., "A chip-to-chip nanoliter microfluidic dispenser," *Lab Chip*, 2009, vol. 9, issue 13,, pp. 1831-1835, with supplemental Material.

Zhang et al., "Miniaturized PCR chips for nucleic acid amplification and analysis: latest advances and future trends," *Nucleic Acids Research*, 2007, vol. 35, No. 13, pp. 4223-4237.

International Search Report and Written Opinion, mailed Dec. 17, 2013, for International Patent Application No. PCT-US2013-062042, 10 pages.

Office Action mailed Aug. 7, 2014, from U.S. Appl. No. 13/843,739 (17 pages).

Wilson et al., Development of an Ibuprofin Lozenge for the Elderly, Drugs Made in Ger., 19950101 Edition Cantor Verlag, DE vol. 38, No. 3, 1995, pp. 90-95.

International Preliminary Report on Patentability, mailed Mar. 31, 2015, for International Patent Application No. PCT-US2013-062042, 6 pages.

\* cited by examiner

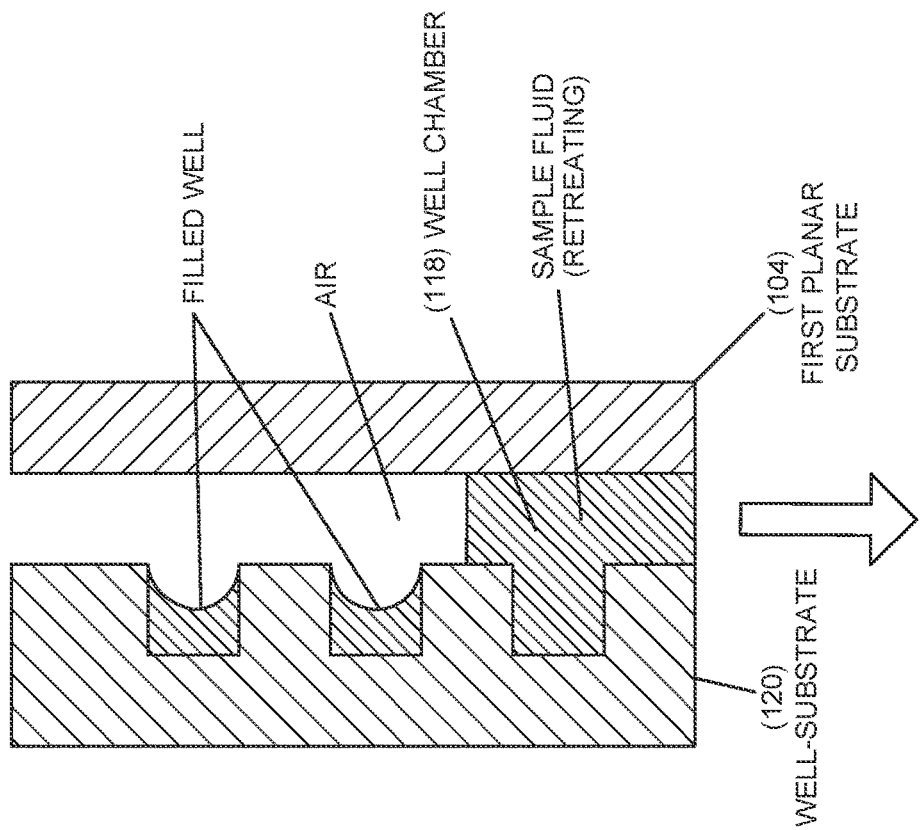
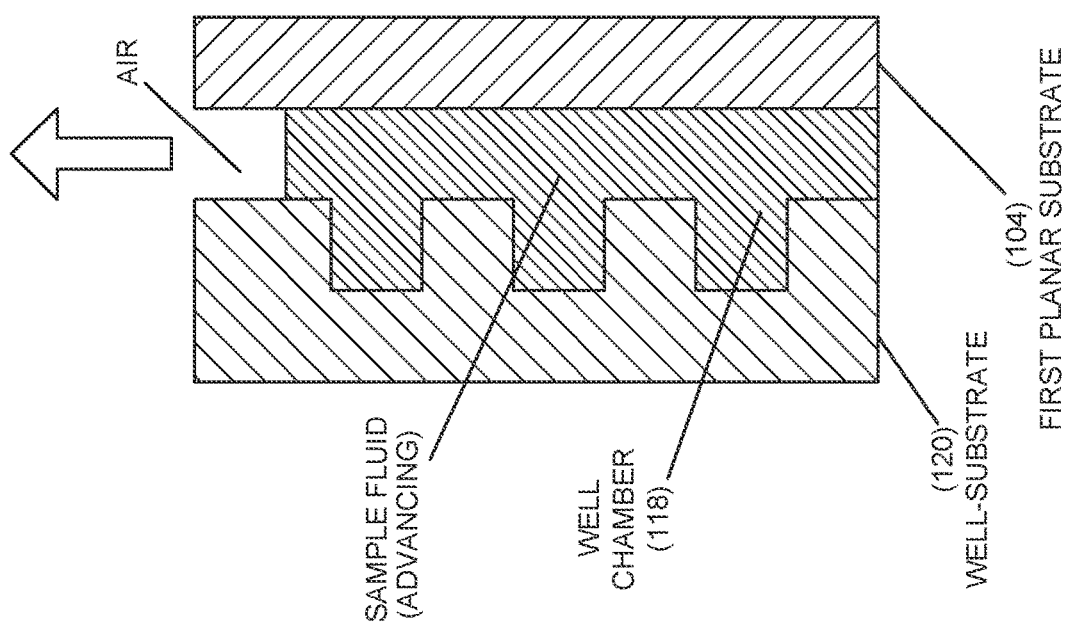
FIG. 4A
FIG. 4B

HONEYCOMB TUBE

This application is a Continuation of U.S. application Ser. No. 16/992,392, filed Aug. 13, 2020, (now U.S. Pat. No. 11,739,383), which is a Continuation of U.S. application Ser. No. 16/230,458, filed Dec. 21, 2018, now U.S. Pat. No. 10,767,226, which is a Divisional of U.S. patent application Ser. No. 14/431,259, filed Mar. 25, 2015, now U.S. Pat. No. 10,190,165, which is a U.S. National Phase of International Application No. PCT/US2013/062042, filed Sep. 26, 2013, which is a continuation of U.S. patent application Ser. No. 13/843,739, filed on Mar. 15, 2013, now U.S. Pat. No. 9,914,968, which claims the benefit of U.S. Provisional Application No. 61/706,115, filed on Sep. 26, 2012. The entirety of each aforementioned application is incorporated by reference herein.

SEQUENCE LISTING

Applicant submits herewith a Sequence Listing in XML format in compliance with 37 C.F.R. §§ 1.831-1.835 and respectfully requests entry thereof. The Sequence Listing in XML format includes no new matter.

BACKGROUND OF THE INVENTION

It can be desirable to perform a plurality of assays simultaneously to provide varied and large data sets. Such a process is often referred to as a "multiplexing assay". Thus, there is a need for devices that can perform multiplexing assays.

BRIEF SUMMARY OF THE INVENTION

Some embodiments of the invention relate to a honeycomb tube that can have a planar frame defining a fluidic path between a first planar surface and a second planar surface. A fluidic interface can be located at one end of the planar frame. The fluidic interface can have a fluidic inlet and a fluidic outlet. The fluidic path further can include a well chamber having a well-substrate configured with a plurality of wells, the well chamber being arranged in the planar frame between the first or second surface and the well-substrate, the well chamber being in fluidic communication with the fluidic inlet and the fluidic outlet.

In some embodiments, the fluidic path can include a pre-amplification chamber arranged in the planar frame between the first and second planar surfaces.

In some embodiments the well chamber is between the pre-amplification chamber and the fluidic outlet.

In some embodiments, the pre-amplification chamber is not included.

In some embodiments, the pre-amplification chamber is a narrow pathway containing one or more chemicals.

In some embodiments, the pre-amplification chamber can include a chamber exit that is in fluidic communication with a well chamber entrance.

In some embodiments, the pre-amplification chamber exit is separated from the well chamber entrance by a passage.

In some embodiments, the pre-amplification chamber exit can be positioned at an upper-most portion of the pre-amplification chamber when the first and second planar surfaces are vertically orientated.

In some embodiments, the well chamber entrance can be positioned at a lower-most portion of the well chamber.

In some embodiments, the well chamber entrance can be positioned beneath the pre-amplification chamber.

In some embodiments, the passage can slope downward from the pre-amplification chamber exit to the well chamber entrance.

In some embodiments, the fluidic path comprises a serpentine channel.

In some embodiments, the fluidic path can be valveless.

In some embodiments, the well-substrate can have a plurality of about 100-to about 1500 nanowells.

In some embodiments, the well-substrate comprises a plurality of wells having a diameter of about 50 to about 500 vim.

In some embodiments, the well-substrate can have a plurality of nanowells each having a depth of about 100 vim.

In some embodiments, the well-substrate can have a plurality of nanowells where each well of the plurality of nanowells can range in depth from 25 µm to 1000 µm.

In some embodiments, the well-substrate can have a plurality of nanowells wherein each well of the plurality of nanowells has a width in the range from about 25 um to about 500 um.

In some embodiments, the well-substrate can have a plurality of nanowells, each well having a volume of about 8.5 nl.

In some embodiments, each well of the plurality of wells can have a volume in the range of about 0.1 nL to 500 nL, In some embodiments, a portion of the planar frame can define an oil chamber for holding a hydrophobic substance.

In some embodiments, the oil chamber can be in fluidic communication with the well chamber.

In some embodiments, the planar frame can be a scaffold extending from a base portion.

In some embodiments, the first and second planar surfaces can have first and second films that fluidically seal the scaffold.

In some embodiments, the planar frame can be fluidically connected to a sample container via the fluidic interface.

In some embodiments, the well-substrate can be constructed from a nickel material.

In some embodiments, the plurality of wells can contain at least one nucleic acid primer and/or probe for amplification and/or detection of a specific target.

In some embodiments, the plurality of wells can contain a molecule, e.g., an antibody or a nucleic acid, for the detection of a specific target.

Some embodiments of the invention relate to a method for providing a sample fluid to a fluidic interface of a honeycomb tube. The honeycomb tube can have a planar frame defining a fluidic path between a first planar surface and a second planar surface, each of which surfaces can be sealed with a thin flexible film. A well-chamber of the fluidic path can be filled with a sample fluid, which comprises a sample material to be analyzed and may further comprise one or more chemicals for carrying out an assay, such that a plurality of wells in the well chamber are filled with the sample fluid. The sample fluid can then be evacuated from the well chamber such that the plurality of wells remains at least partially filled with the sample fluid.

In some embodiments, a pre-amplification chamber is present in the fluidic path before the well chamber, and the reaction fluid undergoes an amplification step in the pre-amplification chamber before filling the well chamber.

In some embodiments, the pre-amplification chamber can include an upper-most exit of the pre-amplification chamber, and the pre-amplification chamber can be filled at a level below the upper-most exit of the pre-amplification chamber.

In some embodiments, the hydrophobic substance is evacuated from the well chamber. In some embodiments, the well chamber is subsequently filled with an aqueous fluid after evacuation of the hydrophobic substance.

In some embodiments, heating and/or cooling cycles are applied to both the first and second planar surfaces.

In some embodiments heating and/or cooling cycles are applied to either the first or second planar surfaces.

Some embodiments of the invention relate to carrying out a multiplex amplification reaction in the honeycomb tube.

In some embodiments, the sample fluid is routed along the fluidic path in a serpentine manner.

In some embodiments, the multiplex reaction involves a nested PCR.

In some embodiments, the multiplex reaction is monitored using fluorescent indicators to indicate the presence of an amplicon.

In some embodiments, the presence of an amplicon is detected using melt-curve analysis.

In some embodiments, the multiplex reaction detects the presence or absence of at least one single nucleotide polymorphism (SNP).

In some embodiments, the sample material used in a multiplex reaction is a body fluid or is derived from a body fluid.

In some embodiments, the sample material is a tissue sample, or is derived from a tissue sample.

In some embodiments, a reaction detects the presence or absence of a protein target.

In some embodiments, a reaction detects the presence or absence of a nucleic acid.

In some embodiments, the nucleic acid is DNA.

In some embodiments, the nucleic acid is mRNA.

In some embodiments, the nucleic acid is microRNA.

BRIEF DESCRIPTION OF THE DRAWINGS

FIGS. 4A-4E show various methods for filling a well-substrate with a sample fluid, according to some embodiments of the invention.

DETAILED DESCRIPTION OF THE INVENTION

I. Exemplary Honeycomb Tube Construction

As used herein, the term "honeycomb" describes a plurality of wells that are set into the surface of a solid substrate at pre-designated locations. In some embodiments, a honeycomb tube of this invention contains at least 100 or 200 wells. In some embodiments, the honeycomb tube can contain any number of wells between about 100 and 300, 400, 500, 600, 700, 800, 900, 1000, 1100, 1200, 1300, 1400, 1500 or more wells. The wells can be of any shape and their locations although predetermined can be arranged in any format or pattern on the substrate. As used herein the term "honeycomb tube" can be used interchangeable with "well chamber," "multi-well reaction chamber," or "multi-well reaction tube".

Figure 1A:
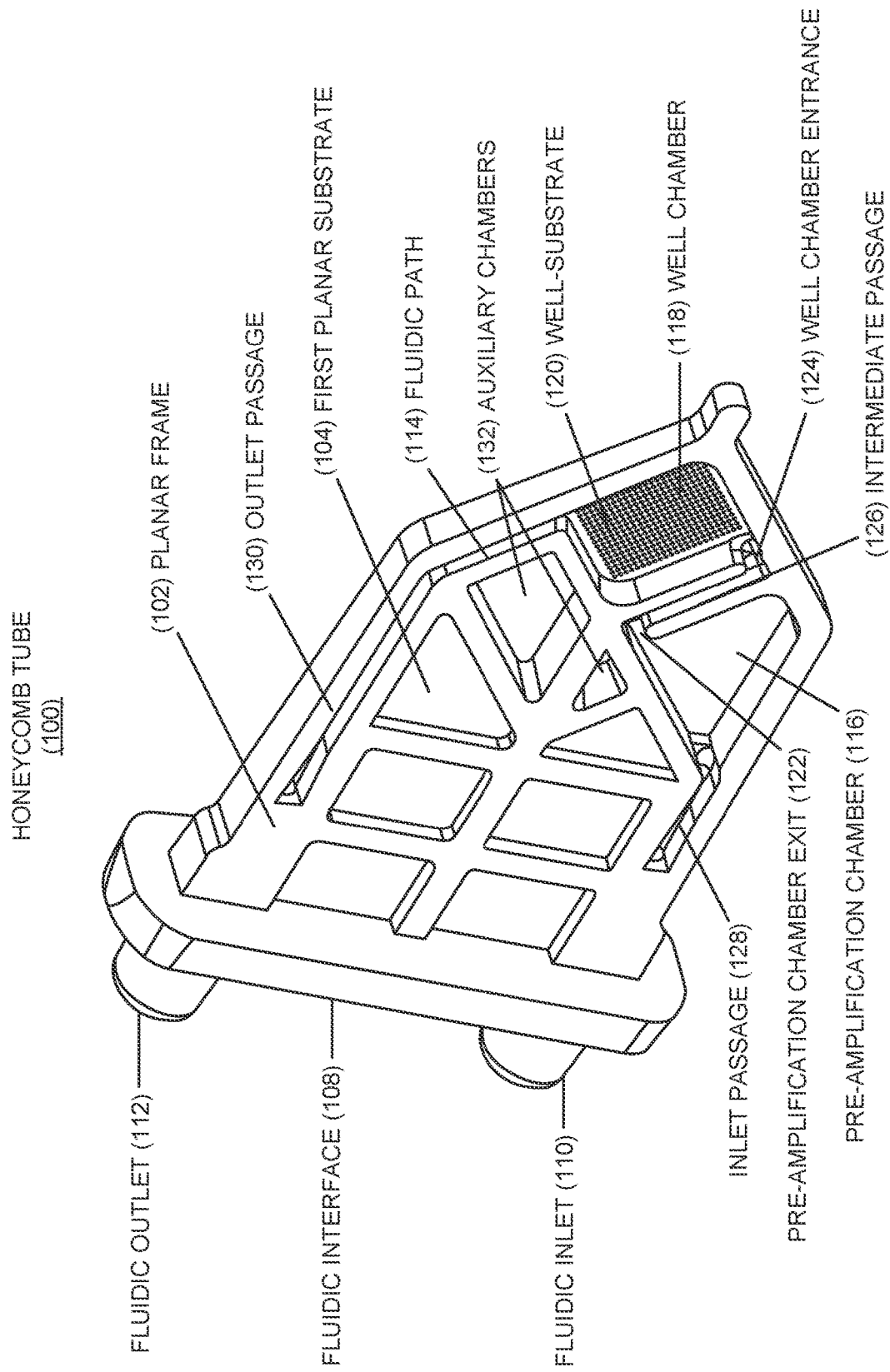
FIGS. 1A, 1B, and 1C respectively show perspective, right-side, and left-side views of a honeycomb tube, according to some embodiments of the invention.
Figure 1B:
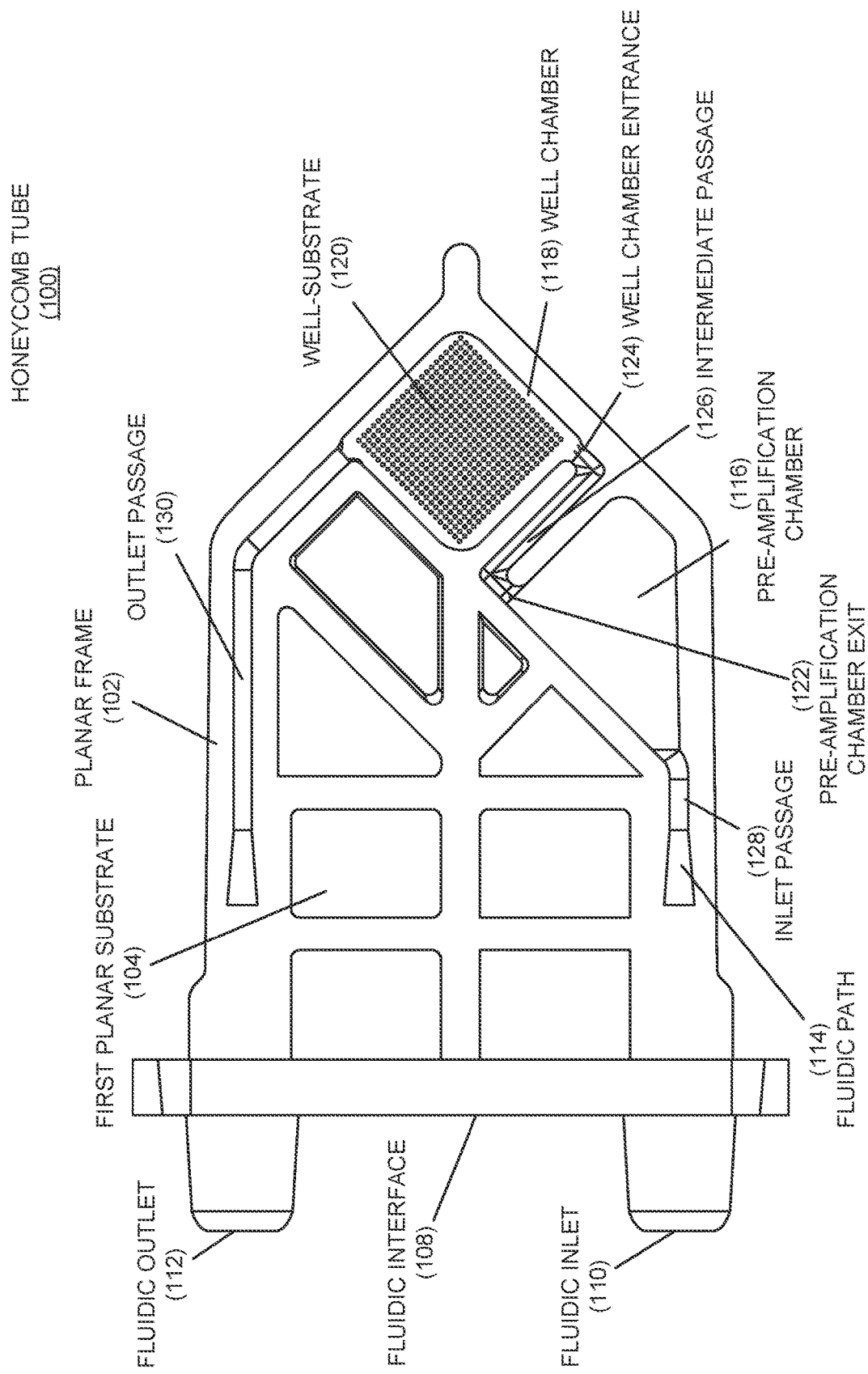
Figure 1C:
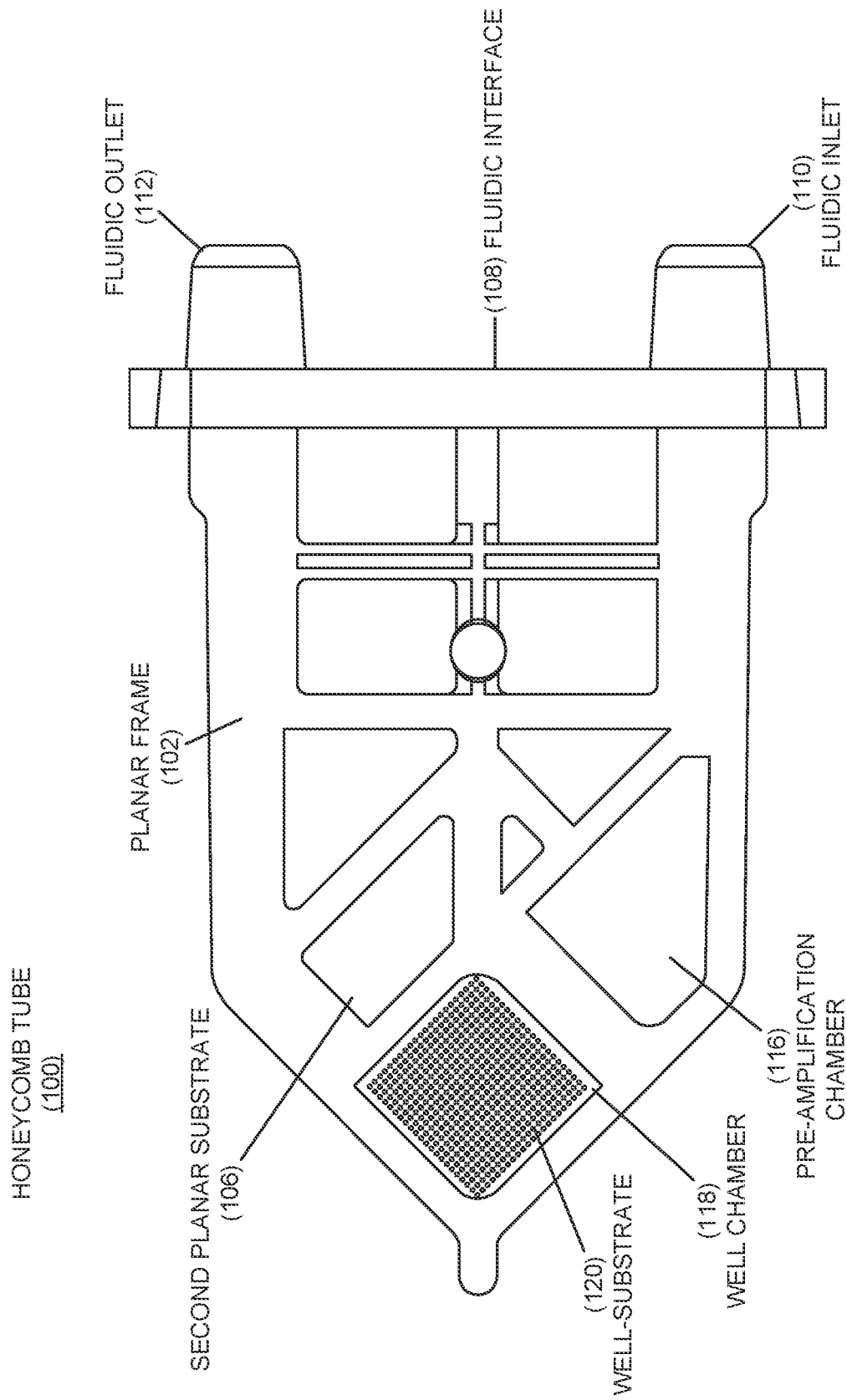

FIGS. 1A, 1B, and 1C respectively show perspective, right-side, and left-side views of a honeycomb tube 100. The honeycomb tube 100 (used interchangeable with a multi-well reaction chamber) includes a planar frame 102, which in some embodiments is a truss-like structure that is formed from polymer (e.g., polypropylene/acrylic substrate) or metal material that is generally PCR compatible. The planar frame 102 can be formed as an open truss or scaffold, bounded on the open sides by a first planar substrate 104 and a second planar substrate 106.

The first planar substrate 104 and second planar substrate 106 can be formed from a relatively thin polymer film that is adhered or otherwise bonded to the planar frame 102. In some embodiments, all or portions of one of the first planar substrate 104 and second planar substrate 106 can be integrally formed with the planar frame 102 (e.g., by 3-D printing, molding, co-molding, or machining one of the substrates with the planar frame 102). In some embodiments, the first planar substrate 104 and second planar substrate 106 are constructed from a transparent material, which is depicted here. Each of the first planar substrate 104 and second planar substrate 106 include interior and exterior facing surfaces. These interior facing surfaces form fluidic passageways with interior cavities of the planar frame 102.

One portion of the planar frame 102 forms a fluidic interface 108. The fluidic interface 108 is a structural member which a majority of the planar frame 102 cantilevers. The fluidic interface 108 can be integrally formed with the planar frame 102. The fluidic interface 108 also serves as a mechanical coupling to a cartridge device, which is described elsewhere herein. The fluidic interface 108 includes a fluidic inlet 110 and fluidic outlet 112, which provide fluidic interfaces to the cartridge device or sample container. Each of the fluidic inlet 110 and fluidic outlet 112 are fluidically coupled to a fluidic path 114 that is formed in the planar frame 102 between the first planar substrate 104 and second planar substrate 106. It should be understood that use of the terms "inlet" and "outlet" do not limit function of the fluidic inlet 110 and fluidic outlet 112. Thus, fluid can be introduced and evacuated from both or either. In some embodiments, the fluidic path 114 is valveless, and thus external increases or decreases in pressures can be applied via the fluidic inlet 110 and fluidic outlet 112 by an external system to move fluid within the fluidic path 114, which extends from the fluidic inlet (110) to the fluidic outlet (112). The cross-section of the fluidic path 114 can be round or rectangular, and can have diameters or widths ranging from about 50 vim to about 2 mm. Typically, the diameters or widths range from about 250 vim to about 1 mm.

The fluidic path 114 includes a pre-amplification chamber 116 that is fluidically connected to a well chamber 118. The well chamber 118 holds a well-substrate 120 (also referred to herein as a honeycomb) having a plurality of wells (also referred to herein as nanowells). The well-substrate 120 can be constructed from a metal, (e.g., gold, platinum, or nickel alloy), ceramic, glass, or other PCR compatible polymer material, or a composite material. The well-substrate 120 includes a plurality of wells. In some embodiments, the well-substrate 120 can include 100-1000 wells, or more. Wells can be formed in a well-substrate 120 as blind-holes or through-holes. The wells can be created within a well-substrate 120, for example, by laser drilling (e.g., excimer or solid-state laser), ultrasonic embossing, hot embossing lithography, electroforming a nickel mold, injection molding, and injection compression molding. In some embodiments, the well-substrate 120 is adhered to or co-molded into the planar frame 102, and in some embodiments the well-substrate 120 is a molded feature of the planar frame 102. In some embodiments individual well volume can range from 0.1 to 1500 nL, typically 0.5 to 200 nL, preferably 0.5 to 50 nL. For example, in some embodiments, each well can have a volume of about 0.1, 0.2.0.3, 0.4, 0.5, 0.6, 0.7, 0.8, 0.9, 1, 1.5, 2, 2.5, 3, 3.5, 4, 4.5, 5, 5.5, 6, 6.5, 7, 7.5, 8, 8.5, 9, 9.5, 10, 11, 12, 13, 14, 15, 16, 17, 18, 19, 20, 15, 30, 35, 40, 45, 50, 55, 60, 65, 70, 75, 80, 85, 90, 95, 100, 110, 120, 130, 140, 150, 160, 170, 180, 190, 200, 225, 250, 275, 300, 325, 350, 375, 400, 425, 450, 475, or 500 nL. Well dimensions can have any shape, for example, circular, elliptical, square, rectangular, ovoid, hexagonal, octagonal, conical, and other shapes well known to persons of skill in the art. Further, well shapes may have cross-sectional areas that vary along an axis. For example, a square hole may taper from a first size to a second size that is a fraction of the first size. In some embodiments, well dimensions can be square, with diameters and depths being approximately equal. In some embodiments, the well diameter and depths are not equal. In some embodiments, walls that define the well are non-parallel. In some embodiments, walls that define the well converge to a point. Well dimensions can be derived from the total volume capacity of the well-substrate 120. In some embodiments, well depths can range from 25 μm to 1000 μm. In some embodiments, for example, wells can have a depth of 25, 50, 75, 100, 150, 200, 250, 300, 350, 400, 450, 500, 550, 600, 650, 700, 750, 800, 850, 900, 950, or 1000 μm. In some embodiments, well diameter can range from about 25 μm to about 500 μm. In some embodiments, for example, the wells can have a width of 25, 50, 75, 100, 125, 150, 175, 200, 225, 250, 275, 300, 325, 350, 375, 400, 425, 450, 475, or 500 μm.

preferably held within the wells, but not on upper surfaces so as to encourage draining of excess fluid.

The wells of the well-substrate 120 can be patterned to have a simple geometric pattern of aligned rows and columns, or patterns arranged diagonally or hexagonally. In some embodiments, the wells of the well-substrate 120 can be patterned to have complex geometric patterns, such as chaotic patterns or isogeometric design patterns as described by Schillinger et al., Computer Methods in Applied Mechanics and Engineering Jan. 22, 2012. The wells can be geometrically separated from one another and/or feature large depth to width ratios to help prevent cross-contamination of reagents during the filling process. In some embodiments, methods as disclosed herein and methods well known to persons of ordinary skill in the art can be used to prevent reagent cross-contamination.

As shown in FIG. 1A, a portion of the well-substrate 120 can be connected to the second planar substrate 106, such that a gap is formed (so as to allow fluid to pass) between a front portion of the well-substrate 120 and the first planar substrate 104. The pre-amplification chamber 116, when present, includes a pre-amplification chamber exit 122, which is located at the upper-most portion of the pre-amplification chamber 116 (in the orientation shown). A well chamber entrance 124 is located at a lower-most portion of the well chamber 118. A down-ward sloping intermediate passage 126 separates the pre-amplification chamber exit 122 and the well chamber entrance 124. A lower-most inlet passage 128 and an upper-most outlet passage 130 make up the remaining portions of the fluidic path 114.

In some embodiments, the planar frame 102 includes one or more (i.e., at least one) of auxiliary chambers 132, which are useable to provide process fluids, such as oil or other chemical solutions to the pre-amplification chamber 116, the well chamber 118, and/or any other portion of the fluidic path 114. Such auxiliary chambers 132 can be fluidically connected to portions of the fluidic path 114 via one or more membranes, valves and/or pressure severable substrates (i.e. materials that break when subjected to a pre-determined amount of pressure from fluid within an auxiliary chamber or adjacent portion of the fluidic path 114) such as metal foil or thin film.

Chart I - Exemplary Well Substrate Dimensions (metric)

| | | | | 25 uL Tube Length (mm) 4.6 | | 65 uL Tube Length (mm) 7.1 | | 100 uL Tube Length (mm) 9.0 | |
|---|---|---|---|---|---|---|---|---|---|
| Diameter (mm) | Depth (mm) | Well volume (nL) | Pitch* (mm$^3$) | # of wells/side | Total Wells | # of wells/side | Total Wells | # of wells/side | Total Wells |
| 0.1 | 0.1 | 0.8 | 0.23 | 20 | 400 | 31 | 961 | 39 | 1521 |
| 0.15 | 0.15 | 2.7 | 0.3 | 15 | 225 | 24 | 576 | 30 | 900 |
| 0.2 | 0.2 | 6.3 | 0.35 | 13 | 169 | 20 | 400 | 26 | 676 |
| 0.25 | 0.25 | 12.3 | 0.4 | 11 | 121 | 18 | 324 | 22 | 484 |

Figure 1D:
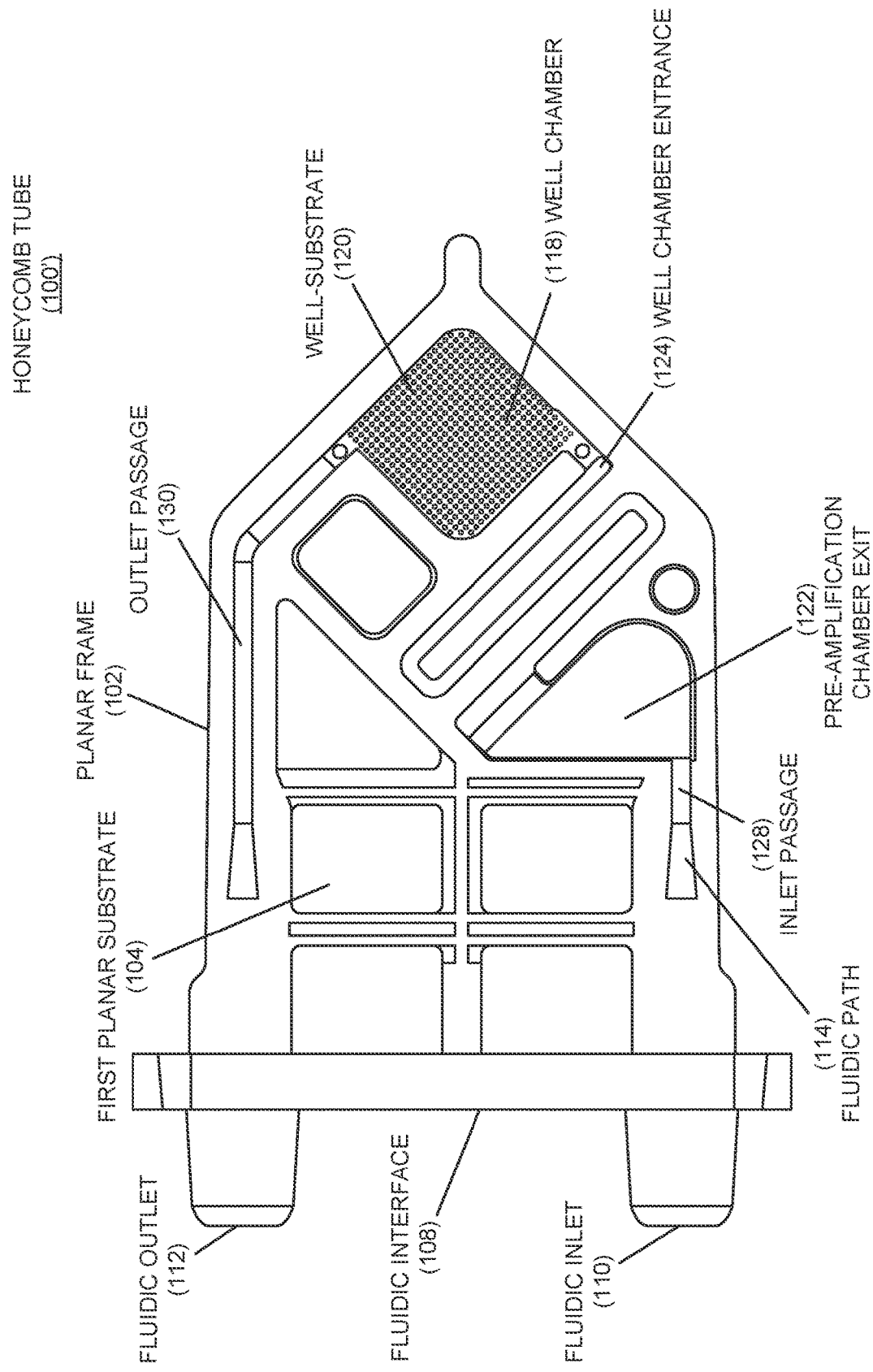
FIGS. 1D and 1E respectively right-side views of honeycomb tubes, according to some embodiments of the invention.

Portions of the well-substrate 120 and/or the interior of the first planar substrate 104 and/or second planar substrate 106 can be modified to encourage or discourage fluid adherence. For example, surfaces defining the wells can be coated with a hydrophilic material (or modified to be hydrophilic), and thus encourage retention of fluid. Further, planar surfaces (surrounding interior surfaces defining the wells) can be coated with a hydrophobic material (or modified to be hydrophobic), and thus discourage retention of fluid thereon. Other surface treatments can be performed such that fluid is In some embodiments, the fluidic path 114 can include torturous portions as shown in FIG. 1D. A torturous path between the inlet passage 128 and the well chamber 118 can be helpful for control and handling of fluid processes. It has been found that a torturous path can help reduce formation of gas bubbles that can interfere with flowing oil through the fluidic path. The honeycomb tube 100' shown in FIG. 1D is largely the same as the honeycomb tube 100 shown in FIGS. 1A-1C, however, the intermediate passage 126' includes a plurality of elongated channel portions connected in a serpentine manner. Here, three elongated channel portions are depicted, however, more or less portions can be used. Generally, at least 2 channel portions are used, and in some embodiments, 2-10 elongated channel portions are used.

Figure 1E:
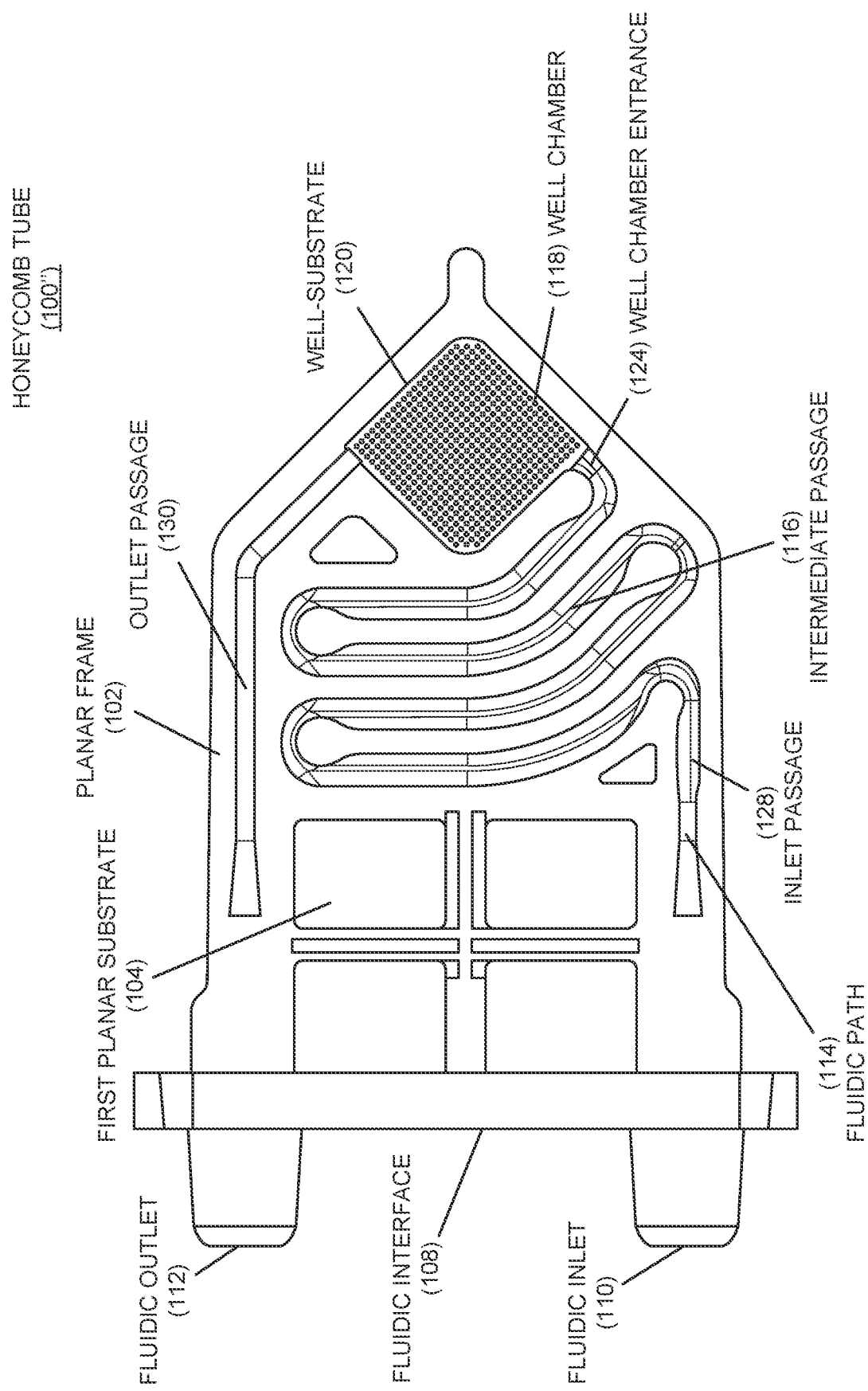

In some embodiments, the fluidic path 114 includes extensive torturous portions, as shown in FIG. 1E. The honeycomb tube 100" shown here is largely the same as the honeycomb tube 100 shown in FIGS. 1A-1C, however, the intermediate passage 126" extends throughout a majority of the structure of the honeycomb tube 100". In this manner, elongated channel portions of the intermediate passage 126' can be made relatively wide to resemble elongated chambers in which amplification can take place. Here, four elongated channel portions are depicted, however, more or less portions can be used. Generally, at least 2 channel portions are used, and in some embodiments, 2-10 elongated channel portions are used. Sharply angled interior curves that define the intermediate passage 126' between the elongated channels are bulbous to reduce cross-sectional area between elongated channels. The reduced cross-sectional area around corners helps to reduce flow rate differentials between fluids at the outer radius of the curve as compared to fluids at the inner radius of the curve. If such flow rate differentials are too great, then unwanted cavitation causing bubble formation can result. Here, the widths of the turns are approximately 50% of the widths of the elongated channel portions. In some embodiments, the widths of the turns are range from 10-90% of the widths of the elongated channel portions. In some embodiments, the widths of the turns vary with respect to one another.

As described above, the channel geometry shown in FIG. 1E can be beneficial for control and handling of fluid processes. Although a pre-amplification chamber is not shown, one or more may be included depending on the particular application of the honeycomb tube 100". It should be understood that with the geometry shown, if a sample includes very few copies of target (i.e. 1 or 2), then after amplification the amplified target may not be mixed and evenly distributed because of the linear nature of the serpentine channel. Thus, it may be necessary to move the fluid back into the cartridge (either into the syringe tube or a separate chamber) to mix and evenly distribute the amplicons before filling the wells of the well chamber.

FIGS. 2A-2G show cross-sections of portions of the honeycomb tube to show various embodiments of the well-substrate 120.

Figure 2A:
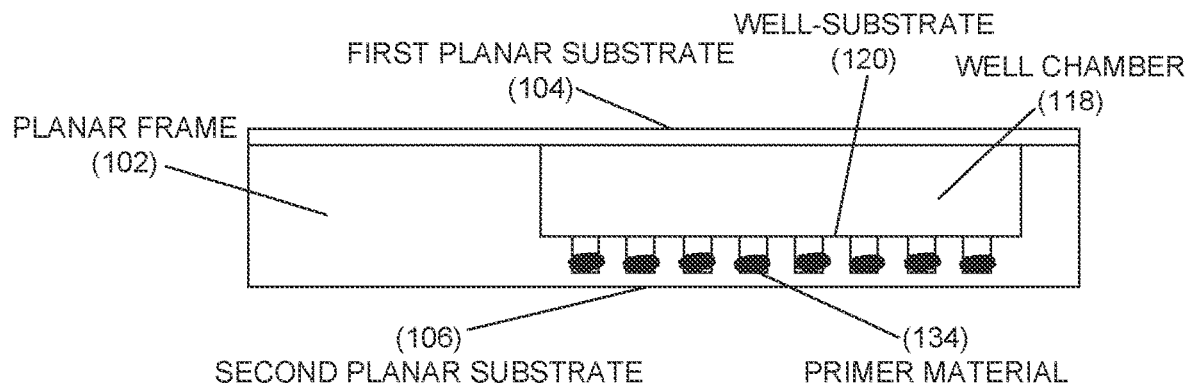
FIGS. 2A-2H show cross-sections of portions of the honeycomb tube to show various embodiments of the well-substrate 120, according to some embodiments of the invention.

FIG. 2A shows an embodiment where wells of the well-substrate 120 are constructed via blind-holes made into the planar frame 102. In this embodiment, the second planar substrate 106 is integrally formed with the planar frame 102, such that they are essentially one piece of material. Primer/probe materials 134 are shown placed into each well of the well-substrate 120.

Figure 2B:
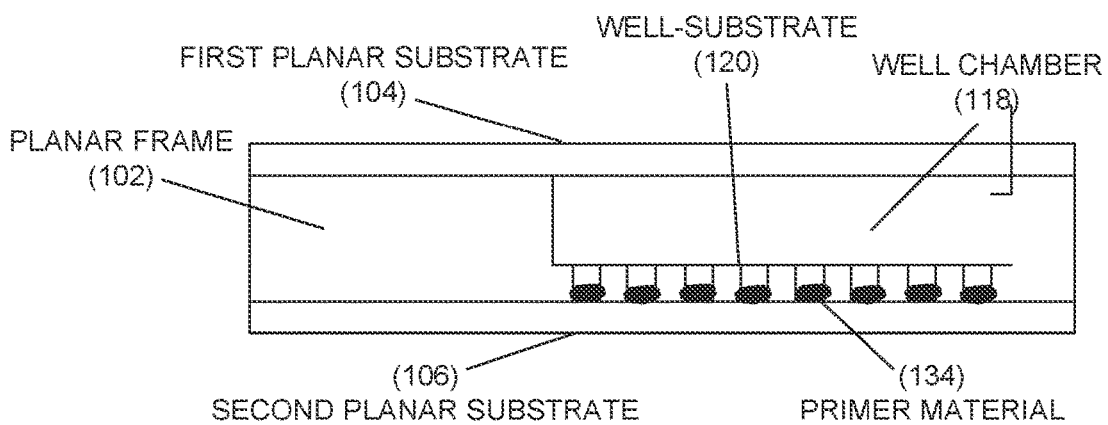

FIG. 2B shows an embodiment where wells of the well-substrate 120 are constructed via through-holes made into a substrate, such as a polymer film, that is bonded onto the planar frame 102. For example, a separate substrate can be drilled to form a well-substrate of through holes, and subsequently adhered or welded onto the planar frame 102. In this embodiment, the second planar substrate 106 is integrally formed with the planar frame 102, such that they are essentially one piece of material. In some embodiments, blind holes can be formed within the second planar substrate 106, which can be bonded onto the planar frame 102.

Figure 2C:
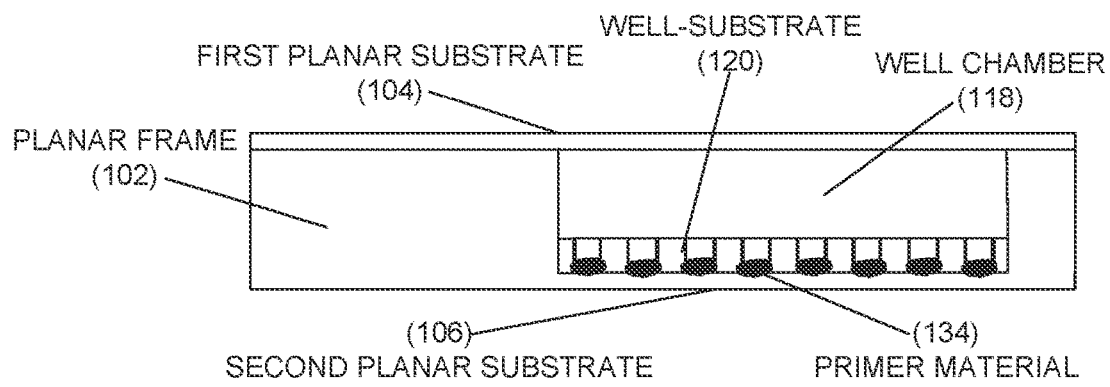

FIG. 2C shows an embodiment where wells of the well-substrate 120 are constructed via through-holes formed within a portion of the planar frame 102. In this embodiment, the second planar substrate 106 is integrated with the planar frame 102 and the well-substrate 120 is a separate component that is adhered or welded to a pocket within the planar frame 102.

Figure 2D:
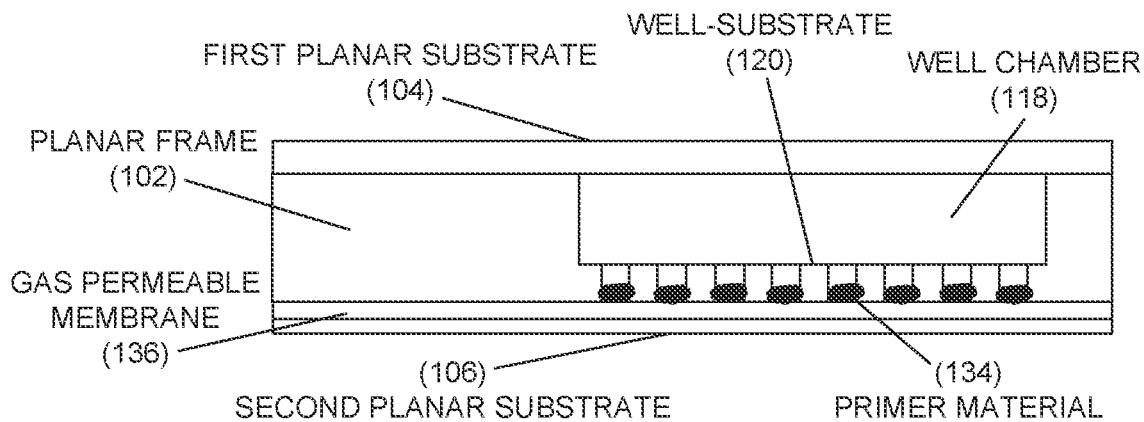

FIG. 2D shows an embodiment where wells of the well-substrate 120 are constructed via through-holes formed within a portion of the planar frame 102, as shown in FIG. 2C. However, in this embodiment, a gas permeable membrane 136 is located between the planar frame 102 and the second planar substrate 106. The membrane 136 enables gas to be evacuated from the wells through the membrane, while not allowing fluid to pass through.

The gas permeable membrane can be adhered to the well-substrate by a gas permeable adhesive. In some embodiments, the membrane 136 is constructed from polydimethylsiloxane (PDMS), and has a thickness ranging from 20-1000 μm, and in some embodiments has a thickness ranging from 100-200 μm.

Figure 2E:
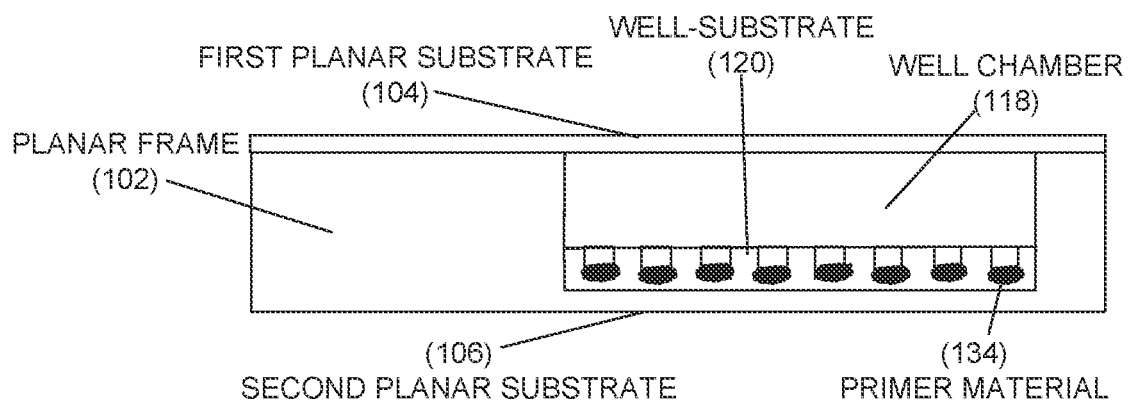

FIG. 2E shows an embodiment where wells of the well-substrate 120 are constructed via blind-holes formed within a portion of the planar frame 102. In this embodiment, the second planar substrate 106 is integrated with the planar frame 102 and the well-substrate 120 is a separate component that is adhered or welded to a pocket within the planar frame 102.

All or portions of the well-substrate 120 can be contain conductive metal portions (e.g., gold) to enable heat transfer from the metal to the wells. For example, the portion of the well-substrate 120 that is placed against the second planar substrate 106 can be a metal plate or coating. In some embodiments, interior surfaces of the wells can be coated with a metal to enable heat transfer.

Figure 2F:
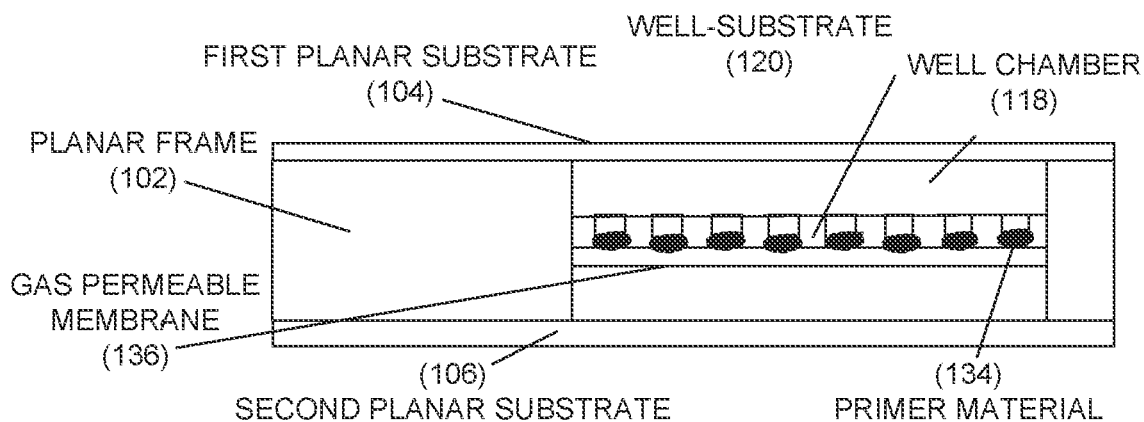
Figure 2G:
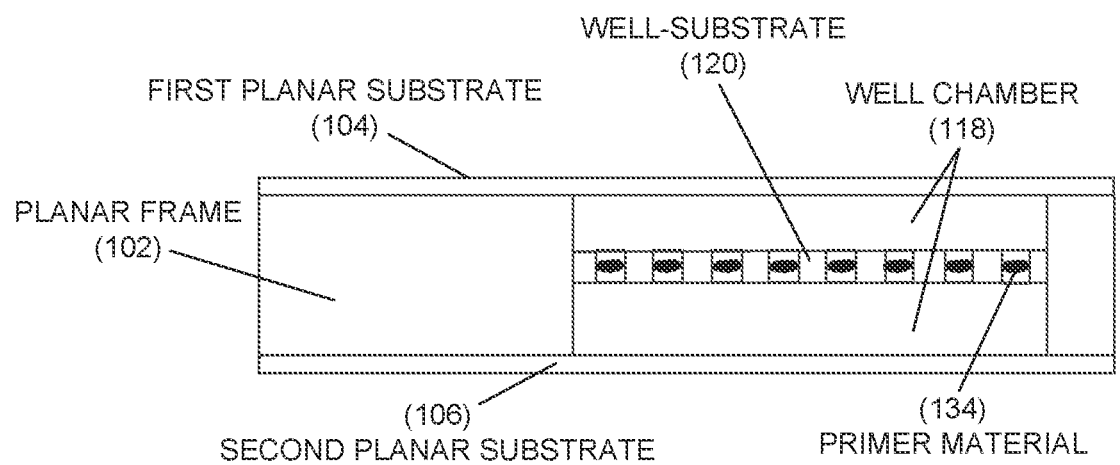

FIG. 2F shows an embodiment that is constructed similarly to the embodiment of FIG. 2D. However, here the well-substrate is positioned a mid-point between the first and second substrates. The gas permeable membrane 136 can be adhered to the well-substrate by a gas permeable adhesive. As with the embodiment shown in FIG. 2D, air can exit through the gas permeable membrane to the back of the wells during liquid filling. After PCR buffer fills the wells and rehydrates the dried primer sets in the wells, an isolation oil or thermally conductive liquid can fill both sides of the well-substrate 120 to prevent cross-talk.

Figure 2H:
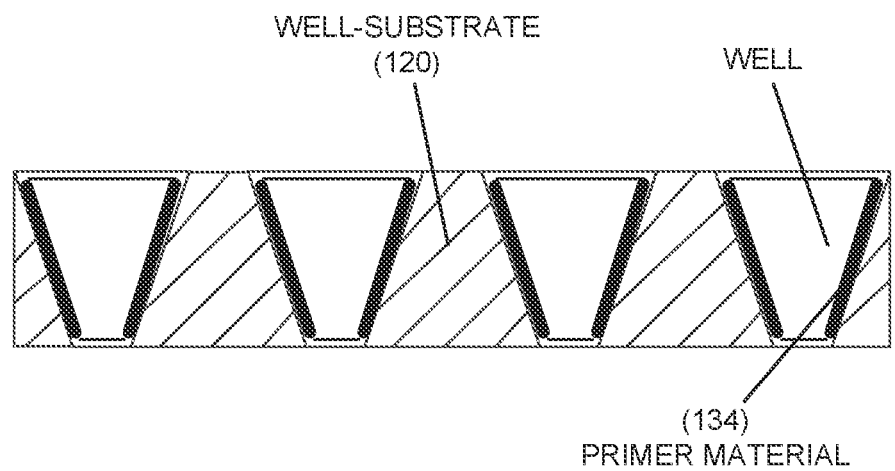

FIG. 2H shows an embodiment that is constructed similarly to the embodiment of FIG. 2F. However, here, a membrane is not included. Thus, processing fluids can be exposed to both sides of the well-substrate 120. After PCR buffer fills the wells and rehydrates the dried primer sets in the wells, an isolation oil or thermally conductive liquid can fill both sides of the well-substrate 120 to prevent cross-talk.

FIG. 2H shows an embodiment of the well-substrate 120 useable with any of the embodiments shown disclosed herein, for example as shown in FIGS. 2A-2F. Here, the wells 121 of the well-substrate 120 is shaped to taper from a larger diameter to a smaller diameter, similar to a cone. It has been found that cone-shaped wells offer an advantage during primer application, because the sloped walls of the wells enable use of a non-contact deposition method (e.g., ink jet) for depositing liquid reagent, which includes the primer material. Further, the cone-shaped wells enable easier application of a liquid reagent for both contact and non-contact methods of liquid reagent application, since the conical shape aids in drying. It has also been found that the cone-shaped wells help prevent bubbles and leaks when the gas permeable membrane 136 is present.

Figure 3A:
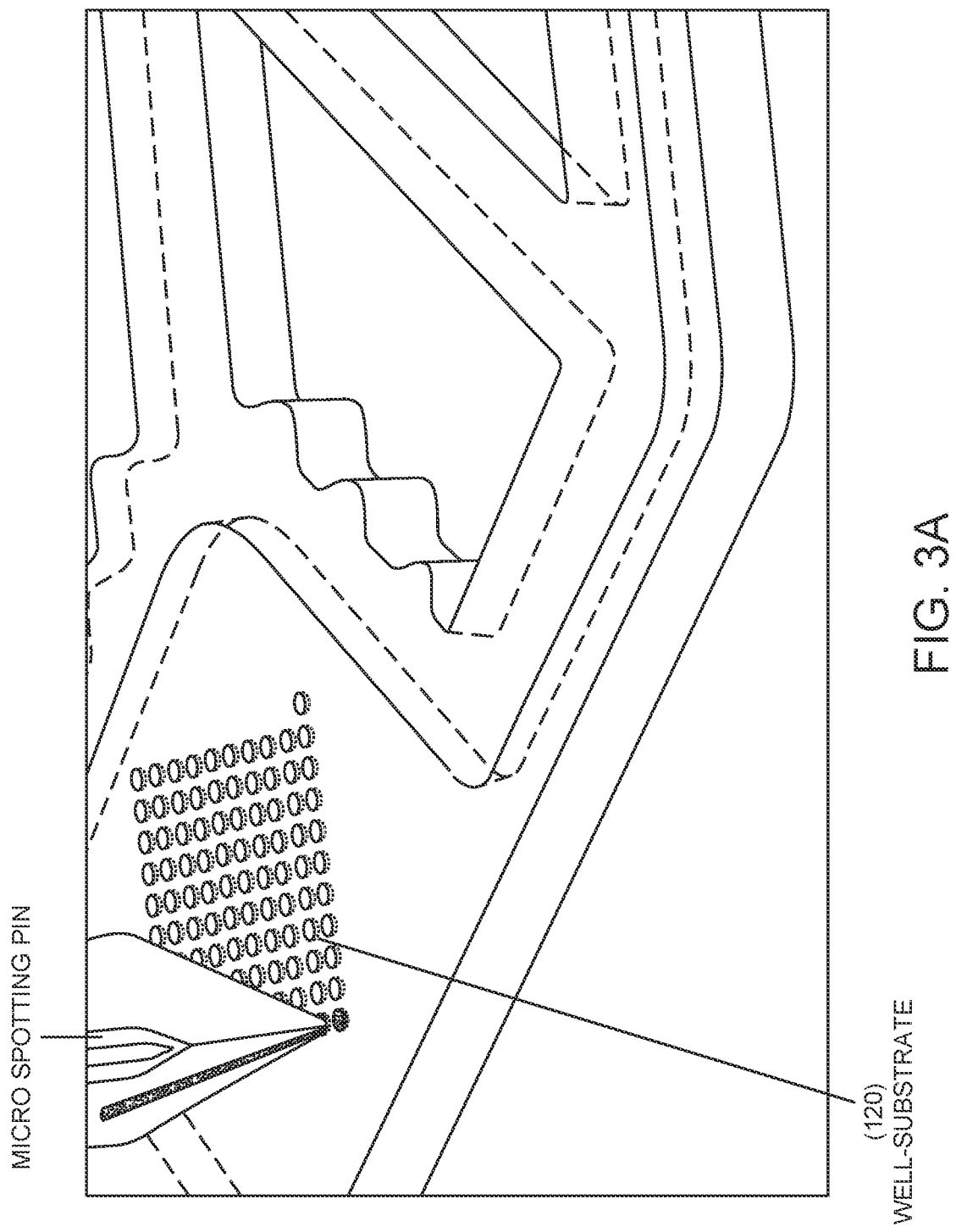
FIG. 3A shows a perspective view of a method for providing the well-substrate 120 with primer material, according to some embodiments of the invention.

FIG. 3A shows a method for providing the well-substrate 120 with primer material. As shown, a commercially available printing pin can be used to fill the wells with a liquid primer, which can be dried in the well or the liquid filled well can be sealed-over after filling. In some embodiments, after the well-substrate 120 is provided with primer in a liquid form, the primer material can be dried such that only a primer residue remains adhering to each well for later liquefaction. Examples of such pins (and associated systems) include the 946MP(x) series of pins from ArrayIt Corporation, located at 524 East Weddell Drive, Sunnyvale, CA 94089, USA. Methods disclosed by Hasan et al., U.S. Pub. No. 2009/0054266 and Hess et al., U.S. Pat. No. 6,716,629, can also be used to provide primer material. During the application process, the printing pin can be configured to make contact with the well-substrate 120. In some embodiments, a non-contact process can be used for providing the liquid reagent (e.g. primer) to the well resulting with dried reagent on one or more walls that define the well, for example a droplet-based method such as ink-jet printing, or other suitable non-contact processes known to persons of skill in the art.

II. Sample Loading into Honeycomb Tubes

Figure 4B:
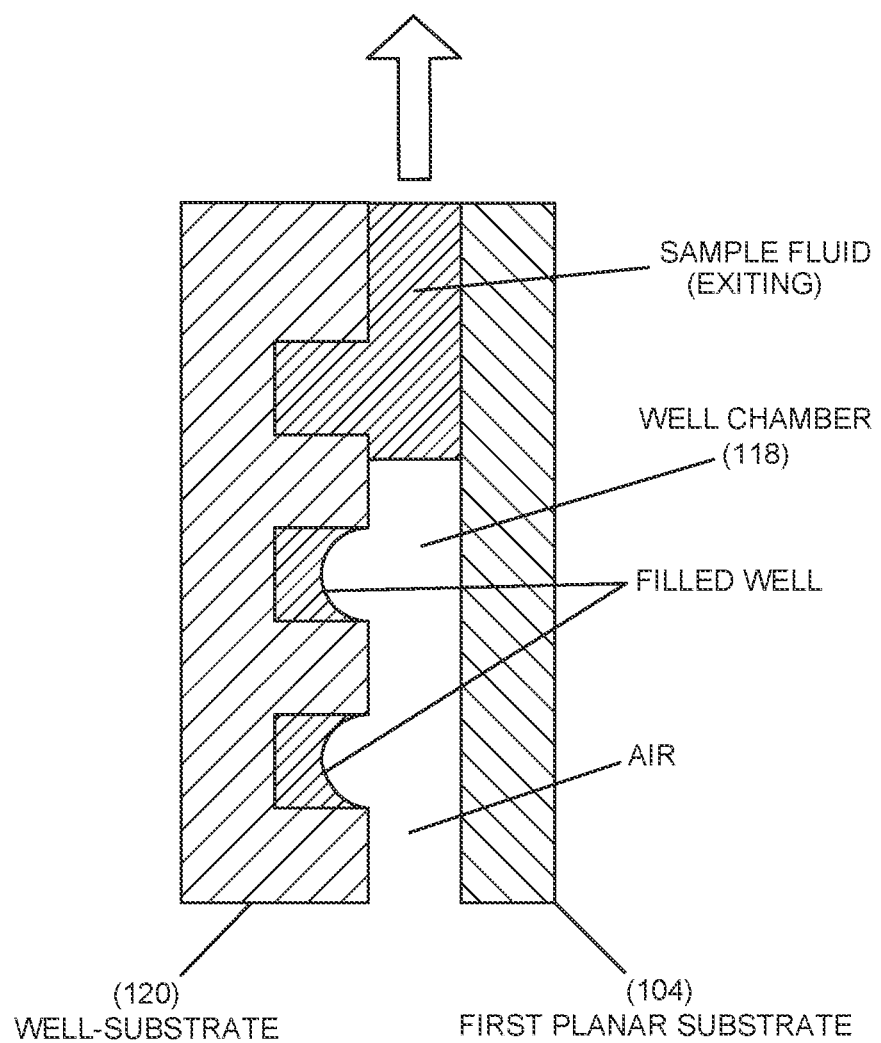

FIGS. 4A and 4B show a method of filling the well-substrate 120 with a sample fluid. In FIG. 4A a sample fluid is advanced (e.g., via pressure) between the well-substrate 120 and the first planar substrate 104. As the fluid passes over the well-substrate 120, each well becomes filled with fluid, which is primarily retained within the wells via surface tension. As recited above, portions of the well-substrate 120, such as the walls defining the wells, can be coated with a hydrophilic substance or treated to become relatively more hydrophilic, and thus encourage complete and uniform filling of the wells as the sample fluid passes over. Additionally, other surfaces of the well-substrate 120, such as top surfaces surrounding the well surfaces, can be coated with a hydrophobic substance or treated to become relatively more hydrophobic such that the fluid sample is only retained in the wells and not on adjacent surfaces thereby reducing inconsistent testing results. Additionally, the interior surface of the first planar substrate 120, can be coated or treated for a hydrophobic effect. In FIG. 4B, it can be seen that only the wells are filled after the sample fluid is retreated. In some embodiments, a fluid sample can be advanced as shown in FIG. 4B', followed by a pocket of air, thus eliminating the need to withdraw the sample as illustrated in the exemplary embodiment shown in FIG. 4B. Filling methods such as "discontinuous wetting" can also be used as disclosed by Jackman et al., Anal Chem., 1998, 70, 2280-2287 and by Hatch et al., MULTILAYER HIGH-DENSITY 3D NANOWELL ARRAYS FOR DIGITAL BIOLOGY, 15th Int'l. Conference on Miniaturized Systems for Chemistry and Life Sciences, Oct. 2-6, 2011, 269-271. Generally, the well-substrate 120 should be de-wetted as quickly as possible to avoid cross-contamination of different primers within the wells.

Figure 4D:
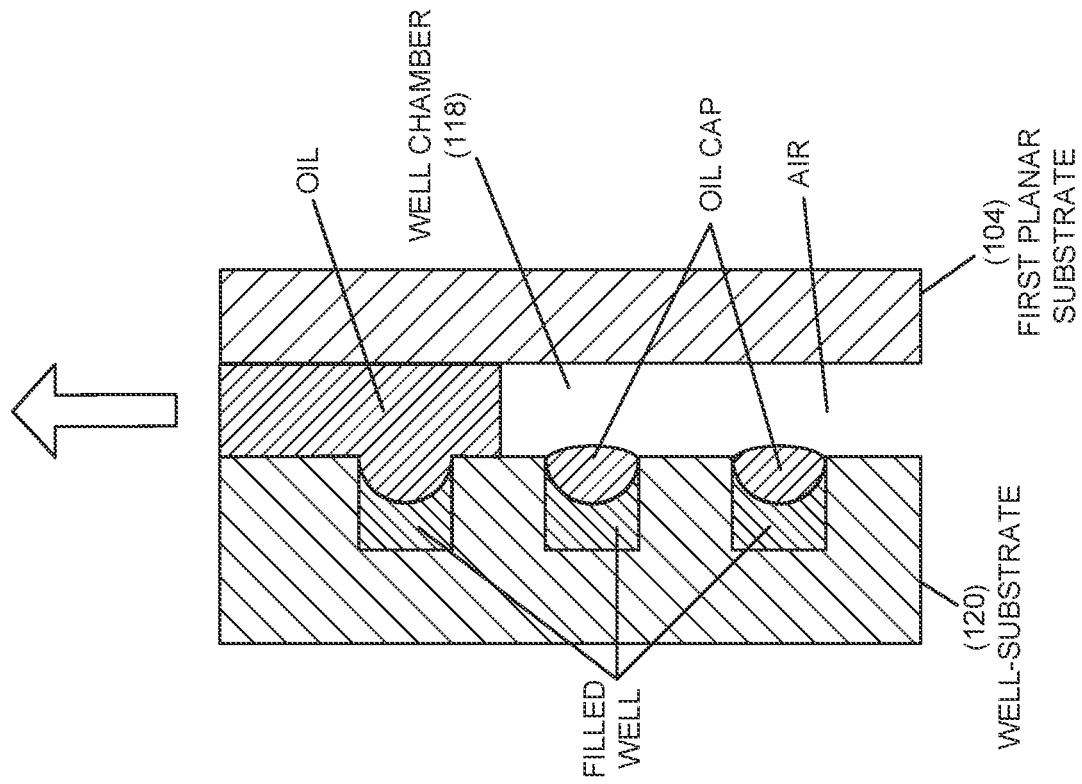
Figure 4C:
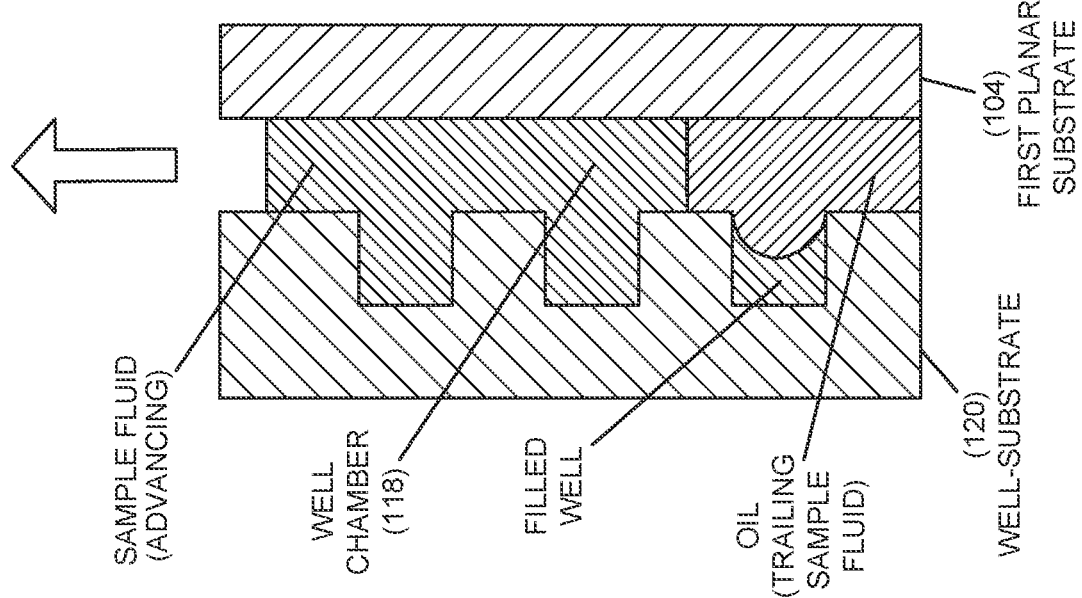
Figure 4D:
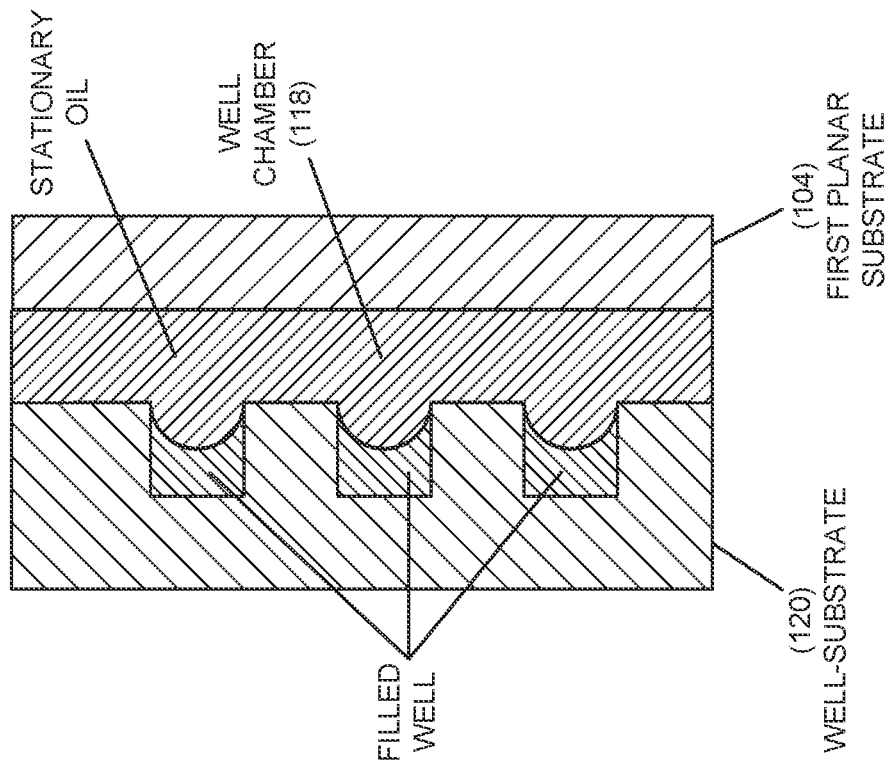
Figure 4D:
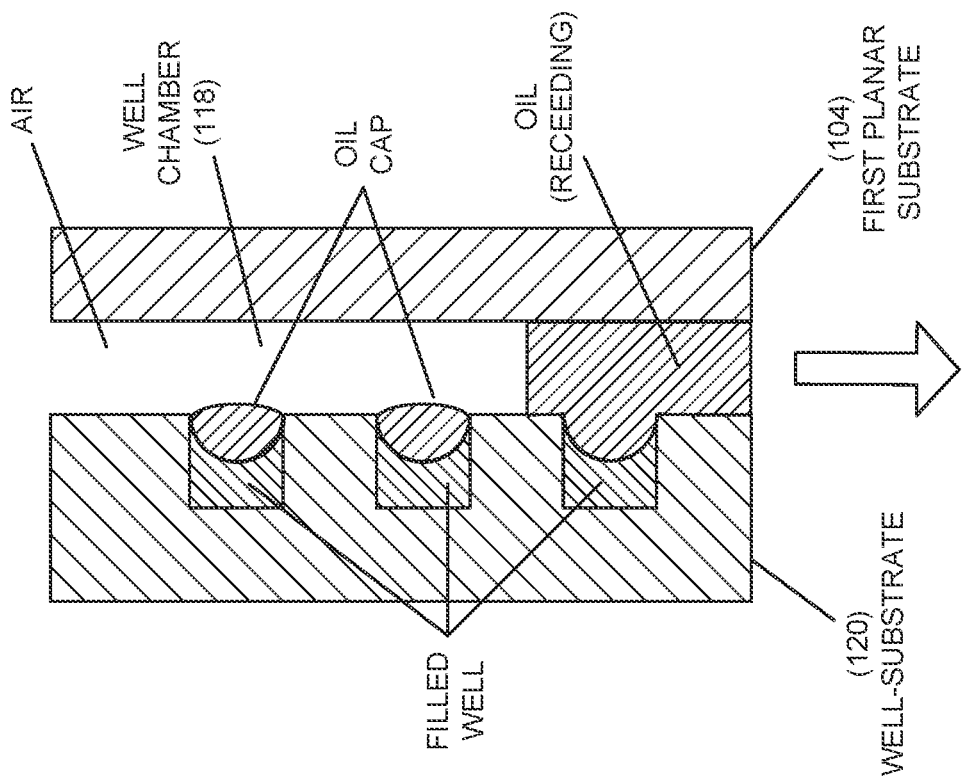

FIGS. 4C and 4D show another method of filling the well-substrate 120 with a sample fluid. In FIG. 4C, the well-substrate 120 is filled according to a combination of the techniques shown in FIGS. 4A and 4B. However, the sample fluid is trailed by a pocket of oil. Although the oil in FIG. 4C is shown directly contacting the sample fluid, an air gap can be provided between the oil cap and the sample fluid.

As shown in FIG. 4D, after each well is filled with sample fluid, the oil can "cap" off each well, which can aid in reducing evaporation when the well-substrate 120 is subjected to heat cycling. In some embodiments, after the wells have been filled, oil can be introduced from the top of the chamber and withdrawn from the chamber entrance 124 as shown in FIG. 4D'. In both of the embodiments shown in FIG. 4D and FIG. 4D', after the wells have been capped with oil, an aqueous solution can fill the chamber 118 to improve thermal conductivity. In some embodiments, the stationary aqueous solution can be pressurized within the chamber 118 to halt the movement of fluid and any bubbles.

In some embodiments, after the wells have been filled, oil can be held stationary within the chamber during heat cycling, as shown in FIG. 4D". In some embodiments, the stationary oil can be pressurized within the chamber 118 to halt the movement of fluid and any bubbles.

Oil such as mineral oil can be used for isolation of each well and to provide thermal conductivity. However, embodiments of the invention are not limited to "oil". Any thermal conductive liquid, such as fluorinated liquids (e.g., 3M FC-40) can be used. Hence, references to "oil" in this disclosure should be understood to include such alternatives.

Figure 4E:
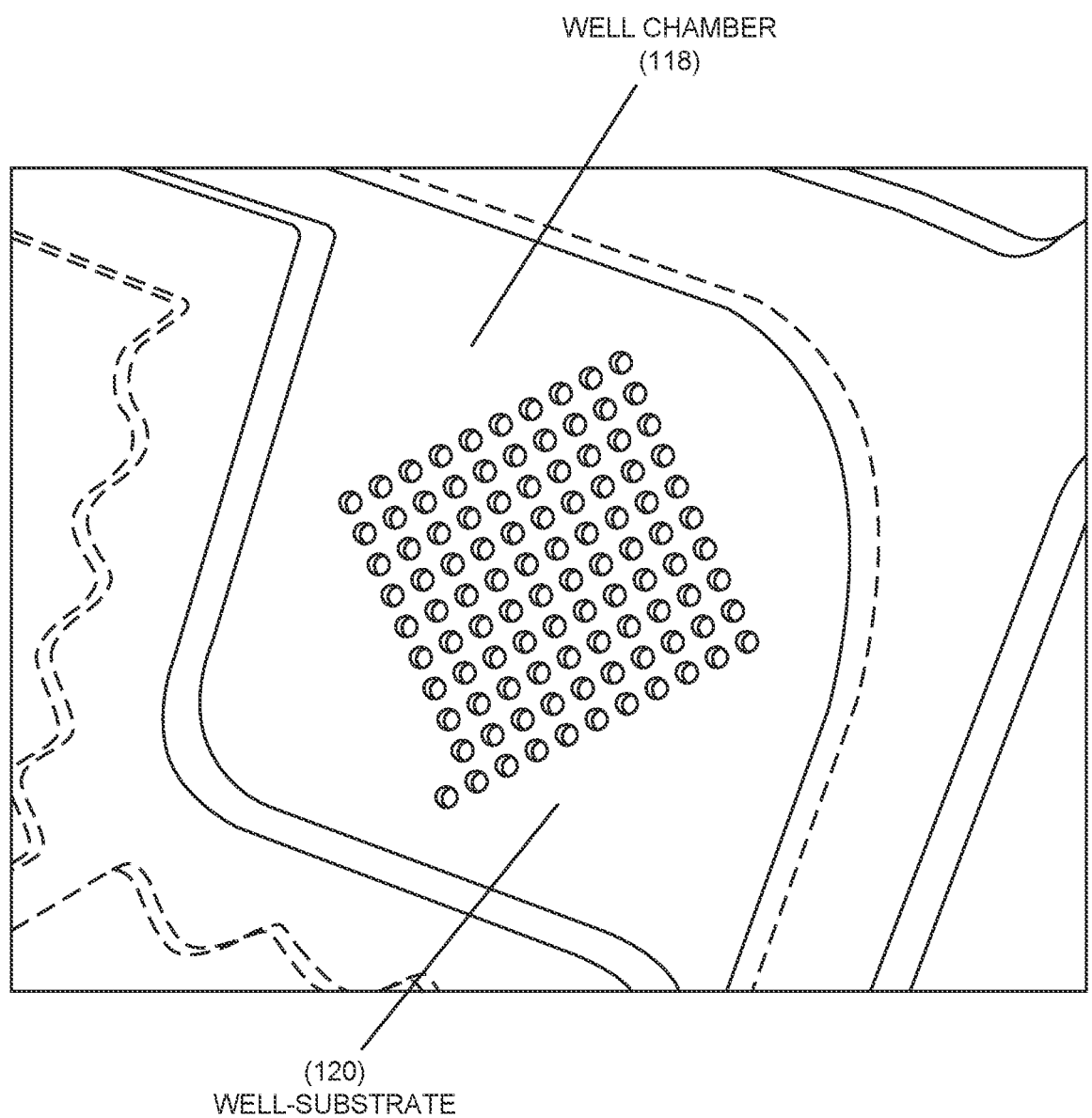

In some embodiments, after the wells have been filled with sample fluid as shown in FIG. 4C, oil can follow the sample fluid to cap the wells and is maintained within the well chamber 118. An experiment detailing this embodiment was performed as described in Example 3 and as shown in FIG. 4E.

Figure 5B:
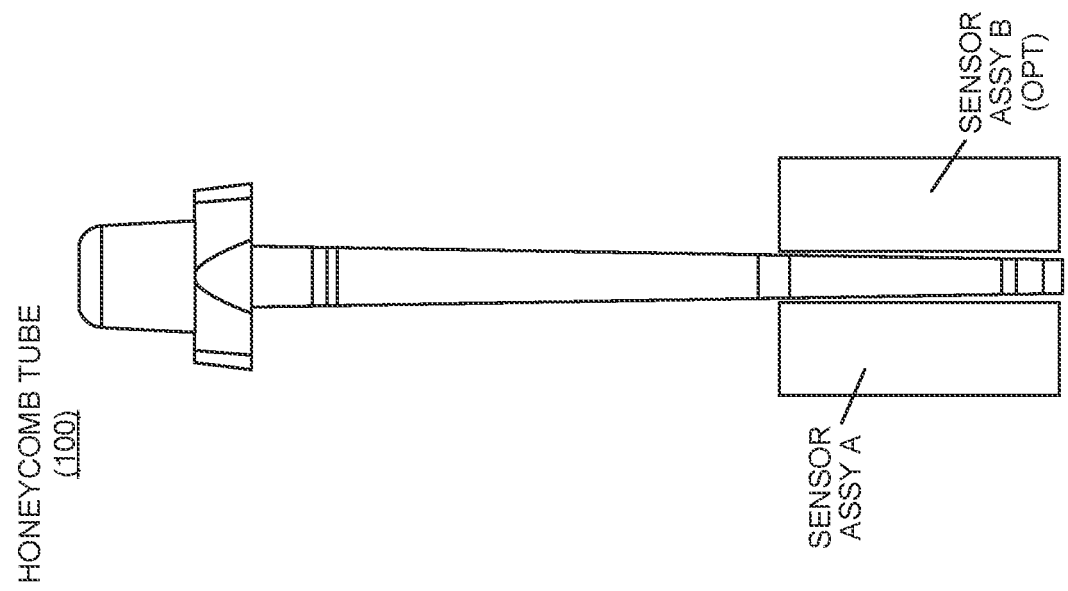
FIGS. 5A-5F show various sensor assemblies positions in relation to a honeycomb tube, according to some embodiments of the invention.
Figure 5A:
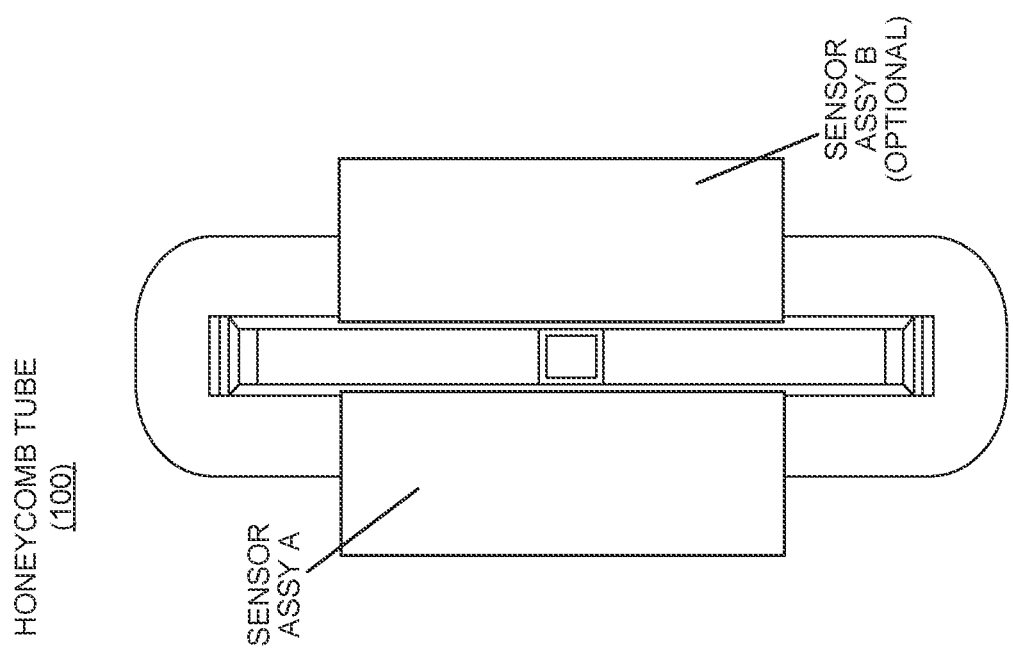

FIGS. 5A and 5B show an exemplary sensor assembly positioning for detecting reactions at the well-substrate 120. In some embodiments, sensor assembly A is positioned directly adjacent or against the first planar substrate 104. In some embodiments, a second sensor assembly B is positioned directly adjacent or against the second planar substrate 106. Each sensor assembly can include excitation and/or detection devices for PCR testing. In some embodiments, the sensors are optical sensors for the excitation and detection of fluorescence.

Figure 5C:
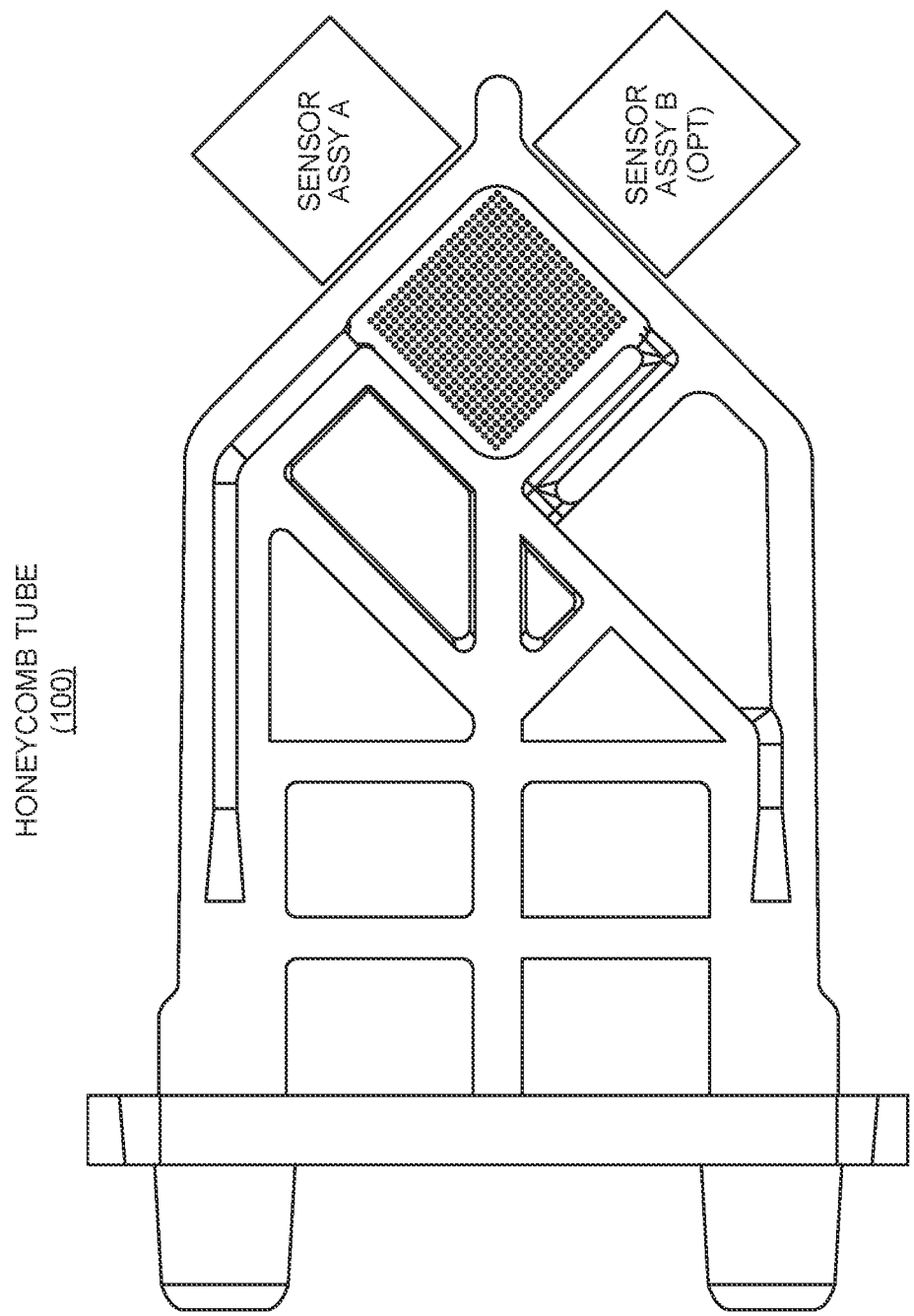

FIG. 5C shows an exemplary sensor assembly configuration that can be used in lieu of or in combination with the configuration of FIGS. 5A and 5B. Here, sensor assembly A is positioned along the forward edge of the honeycomb tube 100. In some embodiments, a second sensor assembly B is included. In some embodiments, one or all of the sensor assemblies A and B of FIGS. 5A and 5B are used in combination with one or all of the sensor assemblies A and B of FIG. 5C.

Figure 5D:
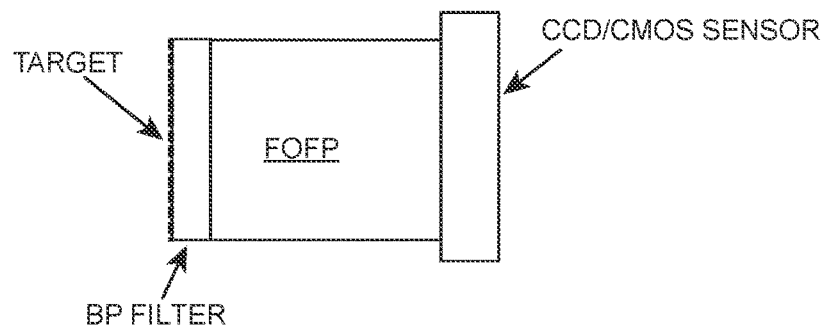
Figure 5E:
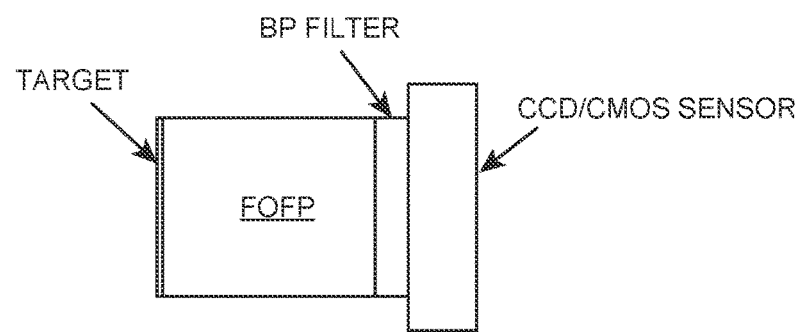

FIG. 5D shows an exemplary sensor assembly configuration. In some embodiments, this sensor assembly configuration can be used in conjunction with the configuration shown in FIGS. 5A-5C. The sensor assembly includes a CCD/CMOS detector coupled to a fiber optic face plate (FOFP). A filter is layered on top of the FOFP, and placed against or adjacent to the target, which here is the well-substrate 120. In some embodiments, the filter can be layered (bonded) directly on top of the CCD with the FOFP placed on top as shown in FIG. 5E.

Figure 5F:
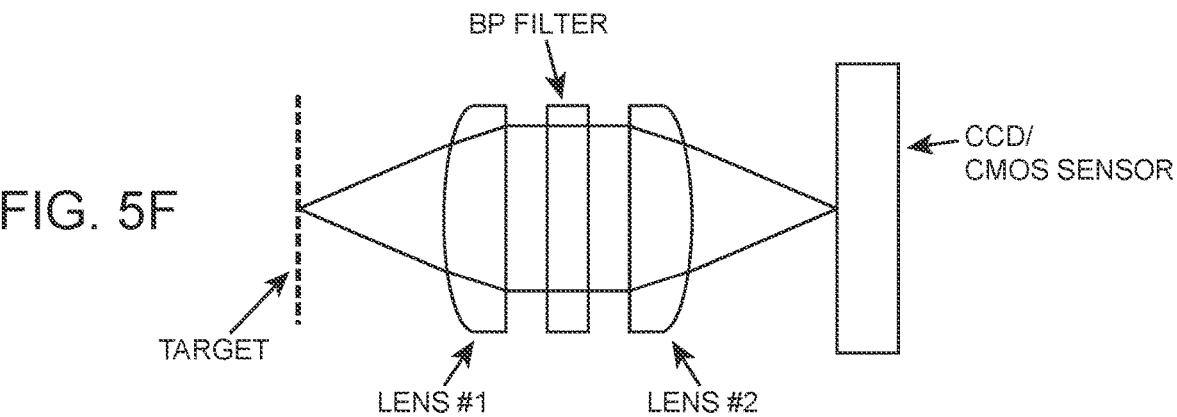

FIG. 5F shows another exemplary sensor assembly configuration. In some embodiments, this configuration can be used in conjunction with one or more of the configurations shown in FIGS. 5A-5C. Here, a CCD/CMOS detector coupled to a double lens configuration with a filter placed in between. In some embodiments, the filter can be bonded to the CCD/CMOS detector.

III. Methods for Use

In some embodiments, a sample fluid is introduced into the fluidic inlet 110 and through inlet passage 128. The pre-amplification chamber 116 can then be filled with the sample fluid. The pre-amplification chamber 116 can include one or more chemicals to cause a desired chemical reaction, and thereby amplify the fluid therein. In some embodiments, the fluid can be maintained within the pre-amplification chamber 116, up to, but not past, the pre-amplification chamber exit 122, until the desired reaction occurs. The fluid is then passed through the pre-amplification chamber exit 122 and into the downward sloping intermediate passage 126. The fluid then passes the well chamber entrance 124 and fills the well chamber 118. In some embodiments, after amplification of the fluid in the pre-amplification chamber, the fluid is withdrawn from the pre-amplification chamber through the fluid inlet and into a separate chamber in the fluid processing cartridge for mixing, and then is returned through the fluid inlet to pass through the pre-amplification chamber to enter the well chamber. The wells of the well-substrate 120 can then be filled, for example, according to a method as shown in FIGS. 4A-4D". Once the wells of the well-substrate 120 are filled, the fluid can be evacuated from the well chamber 118, either through the outlet passage 130, or back through the inlet passage 128. In some embodiments, an oil, such as mineral oil, can be coated over the filled wells to prevent evaporation during thermal cycling. In some embodiments, pressure ranging from 5 to 20 psi will applied to the well-chamber 118. Thus, PCR buffer as well as any thermally conductive liquid (oil) are under compression to hold PCR liquid and any small bubbles—possibly generated during rehydration of the dried primers. This application of pressure can cause immobilization of any generated bubbles, so that no optical interference from moving bubbles and liquid occurs. In some embodiments, a hydration fluid, such as distilled water, can be heated within the pre-amplification chamber 116, or one of the auxiliary chambers 132, such that the well chamber 118 has 100% humidity, or sufficient enough humidity to prevent over evaporation during thermal cycling. After filling is complete, the well-substrate 120 can be heated by an external device that is in thermal contact with the honeycomb tube 100 to perform thermal cycling for PCR. In some embodiments, non-contact methods of heating can be employed, such as RFID, Curie point, inductive, or microwave heating. These and other non-contact methods of heating are well known to persons of ordinary skill in the art and can be readily applied to the honeycomb tube as disclosed herein. During thermal cycling, the honeycomb tube can be monitored for chemical reactions via the sensor arrangements described in FIGS. 5A-5E.

A variety of biological assays can be performed using the honeycomb tube 100, typically for the purpose of indicating the presence of at least one analyte of interest in a test sample. These assays include, but are not limited to, binding assays based on specific binding affinity between a pre-selected pair of molecules (such as an antibody-antigen binding pair or two polynucleotide sequences with sufficient complementarity), nucleic acid amplification reactions relying on certain pre-determined nucleotide sequence-based criteria, and chemical reactions indicative of the presence of molecules of pre-defined activity (such as enzymes).

In some embodiments, analytic agents or probes that are deposited in the honeycomb tube in a pre-determined arrangement, for example, "bait" proteins or nucleic acids, are directly immobilized on the surface of a solid substrate with minimal structural alternation or modification of the substrate surface. In other words, the agents or probes are essentially "spotted" on the surface and arranged and confined within a 2-dimensional space. In some embodiments, the substrate can be manufactured to form an arrangement of multiple wells or indentations of pre-determined dimensions to house the agents or probes, which can be permanently immobilized within the wells or indentations, or temporarily confined within the wells or indentations for the assay time duration. In other words, the analytic probes will be confined within a 3-dimensional space.

Material suitable to serve as analytic probes of the honeycomb tube includes selection of proteins (e.g., full length proteins such as antibodies, protein fragments, or short peptides), nucleic acids (e.g., DNA, RNA, microRNA), carbohydrates, lipids, tissues, cells, or molecules of virtually any and all chemical nature. In other words, any material/molecule that is known to be used to make microarrays for multiplexing assays can be used in the honeycomb testing tube of this invention.

IV. Detection of an Analyte of Interest

One aspect of the present invention relates to the monitoring of an optical signal (using the sensor configurations of FIGS. 5A-5E) indicative of the presence in a test sample of at least one analyte of interest, for example, a target protein (e.g., an antibody of a particular antigenicity), a target cell, a target gene, a target sequence of genes, a target mRNA transcription, or a target nucleic acid. Such target analyte(s) can be of any origin: viral, bacterial, fungal, parasitic (e.g., from a protozoan), animal, or human origin. For example, viral proteins, antibodies against viral antigens, or DNA/RNA sequences derived from a bacterial, or viral genome can be the analytes of interest for detection in test samples. Exemplary non-limiting target analytes can include a nucleic acid sequence such as a micro RNA, mammalian genes, genetic variants of a mammalian gene, such as various genetic mutants, allelic variants, or epigenetic variations (exhibiting different profiles in methylation status) within oncogenes, tumor suppressor genes, or any other genes that have been implicated as relevant to certain diseases and conditions, can be the focus of detection in the application of the honeycomb testing tube of this invention. Exemplary viruses the genes and/or proteins of which can be targets of interest can include but are not limited to human immunodeficiency virus-1 (HIV-1), human cytomegalovirus (CMV), hepatitis C virus (HCV), Hepatitis B virus (HBV), Human Papiloma Virus (HPV), enterovirus, varicella-zoster virus; flaviviruses, hepadnaviruses, herpesviruses, noroviruses, orthomyxoviruses, parvoviruses, papovaviruses, paramyxoviruses, pestiviruses, picornaviruses, and influenza. Exemplary bacteria the genes and/or proteins of which can be targets of detection are *Mycobacterium tuberculosis* (TB), *Bacillus anthracia, Legionella pneumophilia, Listeria monocytogenes, Neisseria gonorrhoeae, Chlamydia trachomatis, Neisseria meningitides, Xtaphylococcus aureus, Helicobacter pylori,* and *Enterococcus faecalis.* Exemplary human genes of potential interest are p53, BRCA1 and BRCA2, Her2/Neu and other EGFR family members, BCR-ABL, PTEN, RAS, RAF, Src, RB, Myc, VEGF, topoisomerase, and the APOEc4 allele.

Basic techniques of detecting and/or quantifying various analytes of interest can be found in, for example, Sambrook and Russell, *Molecular Cloning, A Laboratory Manual* (3rd ed. 2001); Kriegler, *Gene Transfer and Expression: A Laboratory Manual* (1990); Ausubel et al., *Current Protocols in Molecular Biology* (1994); and Harlow & Lane, *Antibodies, A Laboratory Manual* (1988).

For the purpose of detecting the presence of a protein of any particular identity, one can employ a variety of binding affinity-based assays, such as immunological assays. In some embodiments, a sandwich assay format can be performed by capturing a target protein from a test sample with an antibody (which is immobilized to a pre-determined spot in a honeycomb format or confined within a pre-determined well of the honeycomb) having specific binding affinity for the polypeptide. The presence of the protein can then be indicated with a secondary antibody attached to a detectable label, such as a fluorescence-generating molecule.

For the purpose of detecting the presence of a nucleic acid of interest, a probe, or a molecule containing a polynucleotide sequence substantially complementary to the target nucleic acid sequence and capable of hybridizing to the target sequence based on the Watson-Crick base-pairing, is typically used. Again, the probe can be immobilized or spotted to the surface of a solid substrate at a pre-determined location, or in some embodiments, the probe can be confined to a well at a pre-determined location within a predetermined pattern on the substrate. Depending on the nature of the target polynucleotide being detected, for example, whether it is double-stranded or single-stranded, a detection probe can be substantially identical in sequence to the target sequence or substantially identical in sequence to the complementary sequence of the target sequence. In other words, the probe is capable of specially bind to the target nucleotide sequence. In some cases, the probe can contain one binding segment to the target nucleotide as well as a non-binding segment, so long as the presence of the non-binding segment does not interfere with the specific binding between the binding segment and the target nucleic acid. Typically, the binding segment will have at least 8, often at least 10, 12, 15, 20, 25, 30 or even more, contiguous nucleotides that are complementary to either strand of the target polynucleotide sequence, in order to ensure specific recognition of the target sequence. A probe can, in some embodiments, include a light-emitting moiety for easy detection, e.g., a fluorescent or luminescent molecule such as fluorescein, rhodamine, Texas Red, phycoerythrin, hydroxycoumarin, aminocoumarin, cascade blue, Pacific Orange, lucifer yellow, allophycocyanin, TruRed, FluorX, or a lanthanide.

In some embodiments, different fluorescent indicators are employed for indicating the presence of distinct polynucleotide sequences. In some embodiments, a melting point-based detection method can be effective for detecting the presence of distinct target polynucleotide sequences when a common fluorescent indicator is used.

Aside from the binding assay format where detection of an analyte of interest is made directly based on binding affinity of the analyte to the analytic agent provided in the honeycomb tube, an amplification-based assay system for detection and/or quantitation of nucleic acids of interest offers a broad spectrum of applications. In this amplification-based system, one or more nucleic acids of interest is detected and/or quantified upon completion of a sequence-specific amplification reaction. Furthermore, for the purpose of detecting a target nucleic acid by an amplification-based method, multiple sets of primers can be included in each well to permit detection carried out in the nested PCR format, for example, the first set of primers can define a portion of the target sequence and generate an amplicon that allows further amplification by one or more subsequent set of primers.

In some embodiments, the nucleic acid of interest is a DNA molecule. Sequence-specific amplification is performed by providing at least one set of primers, free nucleotides, and appropriate DNA or RNA polymerase in each well of the honeycomb format, and then subjecting the honeycomb tube to appropriate temperatures and time durations to achieve the synthesis and amplification of any target polynucleotide sequence.

Each primer is typically an oligonucleotide (which can be either natural or synthetic) capable, upon forming a duplex with a polynucleotide template by base-pairing, of acting as a point of initiation of nucleic acid synthesis and being extended from its 3' end along the template so that an extended duplex is formed. Extension of a primer is usually carried out with a nucleic acid polymerase, such as a DNA or RNA polymerase. The sequence of nucleotides added in the extension process is determined by the sequence of the template polynucleotide. In most embodiments, primers are extended by a DNA polymerase. Frequently, primers have a length in the range of from 6 to 40 nucleotides, typically from about 12 to about 20 nucleotides. Primers are employed in a variety of nucleic acid amplification reactions, for example, linear amplification reactions using a single primer, or polymerase chain reactions (PCR), employing two or more primers. Guidance for selecting the lengths and sequences of primers for particular applications is well known to those of ordinary skill in the art, see, e.g., Dieffenbach, editor, PCR Primer: A Laboratory Manual, $2^{nd}$ Edition (Cold Spring Harbor Press, New York, 2003).

In the context of a nucleic acid amplification reaction such as a PCR, the amplification product of a target polynucleotide sequence is referred as an "amplicon." Amplicons are a population of polynucleotides resulted from primer extension, usually in the form of double stranded polynucleotides. Amplicons can be produced by a variety of amplification reactions whose products are replicates after multiple rounds of amplification of one or more target nucleic acids. Generally, amplification reactions producing amplicons are template-driven in the base pairing of reactants: both nucleotides and oligonucleotide primers have complements in a template polynucleotide or target polynucleotide sequence. Such complementarity is required for the production of reaction products, or amplicons. In some cases, template-driven reactions are primer extensions with a nucleic acid polymerase or oligonucleotide ligations with a nucleic acid ligase. Such reactions include, but are not limited to, polymerase chain reaction (PCR), linear polymerase reaction, ligase chain reaction (LCR), strand-displacement reaction (SDA), nucleic acid sequence-based amplification (NASBA), rolling circle amplifications, and the like, see, e.g., Mullis et al., U.S. Pat. Nos. 4,683,195; 4,965,188; 4,683,202; and 4,800,159 (PCR); Gelfand et al., U.S. Pat. No. 5,210,015 (real-time PCR using TaqMan probes); Wittwer et al., U.S. Pat. No. 6,174,670; Landegren et al., U.S. Pat. No. 4,988,617 (LCR); Birkenmeyer et al., U.S. Pat. No. 5,427,930 (gap-LCR); Kacian et al., U.S. Pat. No. 5,399,491 (NASBA); Walker, U.S. Pat. Nos. 5,648,211 and 5,712,124 (SDA); Lizardi, U.S. Pat. No. 5,854,033; Aono et al., Japanese Patent Application Publication No. JP 4-262799 (rolling circle amplification); and the like. In some embodiments, amplicons of one or more target nucleic acids are produced by one or more rounds of PCR, e.g., nested PCR, performed in the honeycomb tube of the present invention.

A polymerase chain reaction, or PCR, is an enzyme-mediated reaction for the in vitro amplification of specific DNA sequences by the simultaneous, multiple rounds of primer extensions of complementary strands of DNA. In other words, a PCR is a reaction for making multiple copies or replicates of a target nucleic acid flanked by primer binding sites, such reaction comprising one or more repetitions of the following steps: (i) denaturing the target nucleic acid; (ii) annealing primers to the primer binding sites; and (iii) extending the primers by a nucleic acid polymerase in the presence of nucleoside triphosphates. The reaction is typically cycled through different temperatures optimized for each of the denaturing, annealing, and extension steps. Particular temperatures, time durations at each step, and rates of change between steps depend on many factors well-known to those of ordinary skill in the art, see, e.g., McPherson et al., editors, *PCR: A Practical Approach and PCR2: A Practical Approach* (IRL Press, Oxford, 1991 and 1995, respectively). For example, in a conventional PCR using Taq DNA polymerase, a double stranded target nucleic acid can be denatured at a temperature >90° C., primers annealed at a temperature in the range 50-75° C., and primers extended at a temperature in the range 72-78° C.

The term "PCR" encompasses derivative forms of the reaction, including but not limited to, reverse transcription (RT)-PCR, real-time PCR, nested PCR, quantitative PCR, multiplexed PCR, and other similar variations. For these various PCR assays, typical reaction volumes can range from nanoliters, e.g., about 0.1- to about 500 nL, to microliters, e.g., about 1-about 5 µL, and can be readily contained within the wells of the honeycomb testing tubes of the present invention, thus allowing a rapid multiplexing analysis. In some non-limiting exemplary embodiments, the reaction volume within each of the wells of the honeycomb tube are about 0.1, 0.2, 0.3, 0.4, 0.5, 0.6.0.7, 0.8, 0.9.1, 1.5, 2, 2.5, 3, 3.5, 4, 4.5, 5, 5.5, 6, 6.5, 7, 7.5, 8, 8.5, 9, 9.5, 10, 12, 14, 16, 18, 20, 25, 30, 35, 40, 45, 50, 55, 60, 65, 70, 75, 80, 85, 90, 95, and 100 nL.

A reverse transcription PCR or RT-PCR is a particularly powerful tool for the detection and analysis of RNA in a sample. An RT-PCR is a PCR preceded by a reverse transcription reaction when a target RNA is converted to a complementary single stranded DNA, which is then amplified in the regular PCR process, see, e.g., Tecott et al., U.S. Pat. No. 5,168,038.

A real-time PCR is a PCR process during which the amount of reaction products, i.e., amplicons, is monitored at the same time while the reaction proceeds. There are many forms of real-time PCR that differ mainly in the means of detection used for monitoring the reaction product(s), see, e.g., Gelfand et al., U.S. Pat. No. 5,210,015 (TaqMan probes); Wittwer et al., U.S. Pat. Nos. 6,174,670 and 6,569,627 (intercalating dyes); Tyagi et al., U.S. Pat. No. 5,925,517 (molecular beacons). Detection chemistries for real-time PCR are reviewed in Mackay et al., *Nucleic Acids Research*, 30: 1292-1305 (2002).

A nested PCR is a PCR process that involves at least two stages of amplification where the amplicon of a first stage PCR using a first set of primers becomes the template for a second stage PCR using a second set of primers. At least one primer of the second set of primers has sequence complementarity and can hybridize to the target polynucleotide sequence at a location that is between the hybridization sites of the two primers of the first set, i.e., at a location within the sequence of the amplicon of the first stage PCR.

A multiplexed PCR is a PCR process where amplification of multiple potential target polynucleotide sequences are simultaneously carried out in the same reaction mixture, see, e.g., Bernard et al., *Anal. Biochem.*, 273: 221-228 (1999) (two-color real-time PCR). The honeycomb assay format of the present invention is suitable for carrying out multiplexed PCR. A distinct set of primers is contained in a well-intended for the amplification and detection of a distinct target polynucleotide sequence. Typically, there are a number of repeat wells containing the same primers as duplicate wells in the honeycomb well arrangement. For example, in a non-limiting exemplary embodiment, one entire honeycomb well arrangement can include different pre-made reaction mixtures each containing a distinct primer set selected from a total of up to 8, 16, 25, 50 or even 100 different sets of primers, with a cluster of 8 replicate wells provided for each reaction mixture containing a distinct set of primers.

A quantitative PCR is a PCR process that allows one to measure the abundance of one or more specific target sequences in a sample. Quantitative PCRs can involve measuring both absolute quantitation and relative quantitation of the target sequences. Quantitative measurements are made using one or more reference sequences that can be assayed separately or together with a target sequence. The reference sequence can be endogenous (naturally existing) or exogenous (artificially added) to a sample, and in the latter case, can comprise one or more competitor templates. Typical endogenous reference sequences include segments of transcripts of the following genes: β-actin, GAPDH, $β_2$-microglobulin, ribosomal RNA, and the like. Techniques for quantitative PCR are well-known to those of ordinary skill in the art, see, e.g., Freeman et al., *Biotechniques*, 26: 112-126 (1999); Becker-Andre et al., *Nucleic Acids Research*, 17: 9437-9447 (1989); Zimmerman et al., *Biotechniques*, 21: 268-279 (1996); Diviacco et al., *Gene*, 122: 3013-3020 (1992); Becker-Andre et al., *Nucleic Acids Research*, 17: 9437-9446 (1989).

An amplification reaction can be a "real-time" amplification when a detection mechanism is present that permits a reaction product to be measured at the same time as the amplification reaction progresses, e.g., real-time PCR described above, or real-time NASBA as described in, e.g., Leone et al., *Nucleic Acids Research*, 26: 2150-2155 (1998). As used herein, the term "amplifying" means performing an amplification reaction. A "reaction mixture" is a solution (or a lyophilized version of such solution) containing all the necessary reactants for performing a reaction, which can include, but are not be limited to, buffering agents, salts, co-factors, scavengers, and the like. In some embodiments, a dried reagent is deposited in a well of the honeycomb tube during manufacturing process. In some embodiments, the dried reagent contains at least one set of primers for amplification of one or more target polynucleotide sequences, nucleoside triphosphates, enzyme(s), and/or a detection moiety that indicates the presence and/or quantity of one or more amplicons. In some embodiments, the detection moiety is a fluorescent indicator. Detection or quantification of amplicons in a real-time PCR often involves the use of a fluorescence resonance energy transfer probe, or a FRET probe, such as a TaqMan® probe, a Molecular beacon probe, or a Scorpion probe.

As used herein, a fluorescent indicator is a molecule (e.g., a dye, or a probe) that is capable of generating a fluorescent signal in the presence of a product or products of an amplification reaction (i.e., an amplicon) such that as the amplicon accumulates in the reaction mixture the signal of the fluorescent indicator increases, at least over a predetermined range of amplicon concentrations.

Several types of fluorescent indicators can be used in the amplification reactions performed in the honeycomb tubes of this invention: first, a fluorescent dye can be used. Suitable dyes of this class are non-specific with regard to the polynucleotide sequence of the amplicon, such as intercalating dyes that bind to double-stranded DNA products, for example, ethidium bromide, SYBR Green I and II, SYBR Gold, YO (Oxazole Yellow), TO (Thiazole Orange), and PG (PicoGreen), see, e.g., Ishiguro et al., *Anal. Biochem.*, 229: 207-213 (1995); Tseng et al., *Anal. Biochem.*, 245: 207-212 (1997); Morrison et al., *Biotechniques*, 24: 954-962 (1998). Additional fluorescent indicators suitable for use with the invention are well known to persons of ordinary skill in the art.

Second, in some cases one or more primers can be designed to having a hairpin structure with a fluorescent molecule held in proximity to a fluorescent quencher, such that the fluorescence is quenched by the quencher until the hairpin structure is forced apart by primer extension, see, e.g., Whitecombe et al., *Nature Biotechnology*, 17: 804-807 (1999) (Amplifluor primers). Suitable fluorescent molecules include those mentioned in an earlier section.

Third, fluorescent indicators also can be specific for the polynucleotide sequence of a target nucleic acid. Often referred to as fluorescent probes, this type of indicators usually comprise a fluorescent moiety in proximity to a fluorescent quencher until an oligonucleotide moiety to which they are attached specifically binds to an amplification product, see, e.g., Gelfand et al., U.S. Pat. No. 5,210,015 (TaqMan probes); Nazarenko et al., *Nucleic Acids Research*, 25: 2516-2521 (1997) (scorpion probes); Tyagi et al., *Nature Biotechnology*, 16: 49-53 (1998) (molecular beacons). Fluorescent indicators can be used in connection with real-time PCR, or they can be used to measure the total amount of reaction product at the completion of a reaction. For a review of various molecular beacons and other hairpin probes, see Broude, *Encyclopedia of Diagnostic Genomics and Proeomics*, 2005, pages 846-851.

Typically, for each reaction performed in the honeycomb tubes of this invention, regardless of its nature of being binding affinity-based or amplification-based, there will be at least one positive control and at least one one negative control, such that these controls will yield confirmation of a successful reaction: any positive signal detected is not due to a system-wide contamination, and any negative signal detected is not due to the failure of the assay system. In some embodiments, an internal standard can be included. An internal standard is a known molecule that participates in the same reaction, for example, a nucleic acid sequence that is amplified in the same amplification reaction as a target polynucleotide, in order to allow quantification (either relative quantification or absolute quantification) of the target analyte in a sample. An internal standard can be endogenous, i.e., known to be pre-existing in a sample, or exogenous, i.e., added prior to testing.

V. Designing Analytic Agents to Accommodate Reaction Conditions

Because the multiplexing assays to be performed in the honeycomb tubes of this invention are typically carried out at approximately the same conditions at approximately the same time, the analytic agents located on each spot or within each well of the honeycomb tube must be carefully designed in order to achieve optimal or near optimal reaction results under a set of pre-determined reaction parameters. In one example, 8 different polynucleotide probes are spotted or immobilized on a substrate surface for detecting 8 distinct target nucleic acids in a sample by virtue of sequence complementarity-based hybridization. It is well within the skill of an ordinary artisan to design and optimize each target probe sequence to fall within the pre-determined reaction parameters for a particular assay. In designing and optimizing a probe, non-limiting parameters include probe length, relative location within the target sequence, and GC content that will result specific hybridization between the probe and its target under the given reaction conditions for a particular assay.

In another example, 8 sets of different reaction mixtures intended for amplification of 8 different target polynucleotide sequences are arranged in a 4-patch format, each patch containing 8 replicate spots of each reaction mixture. Each of these 8 sets of different reaction mixtures contains at least one set of oligonucleotide primers for amplification of a distinct target sequence. These 8 sets of primers can be designed such that the denaturing, annealing, and extension steps can all be completed adequately for 8 different target sequences under the same temperatures and during the same time frame.

A skilled artisan will be able to accomplish the necessary design by adjusting the length, GC-contents of the probes or primers. In some cases, substituting naturally occurring nucleotides with modified or artificial nucleotides is effective to further fine-tune the annealing/denaturing behavior of the probe and primers. See, e.g., Leconte et al. *J Am Chem Soc.* 2008; 130(7):2336-2343; U.S. Pat. No. 8,268,978. Some known analogs include 1-methyladenine, 1-methylinosine, 1-methylpseudouracil, 1-methylguanine, 2-methyladenine, 2-methylguanine, 2-thiocytosine, 2-thiocytosine, 2-thiouracil, 2,2-dimethylguanine, 2,6-diaminopurine, 2-methylthio-N6-isopentenyladenine, 3-methylcytosine, 4-acetylcytosine, 4-thiouracil, 5-bromouracil, 5-carboxymethylaminomethyl-2-thiouracil, 5-(carboxyhydroxylmethyl) uracil, 5-carboxymethylaminomethyluracil, 5-fluorouracil, 5-methylcytosine, 5-methoxyuracil, 5-methylaminomethyluracil, 5-methyl-2-thiouracil, 5-methyluracil, 5'-methoxycarbonylmethyluracil, 5-methoxyaminomethyl-2-thiouracil, 7-methylguanine, 8-hydroxy-N6-methyladenosine, aziridinylcytosine, beta-D-mannosylqueosine, dihydrouracil, inosine, N6-isopentenyladenine, N6-methyladenine, N-uracil-5-oxyacetic acid methylester, oxybutoxosine, pseudoisocytosine, pseudouracil, pseudouracil, queosine, uracil-5-oxyacetic acid, uracil-5-oxyacetic acid methylester, and uracil-5-oxyacetic acid etc. Many nucleotide analogs are commercially available through suppliers such as Sigma and Applied Biosystems.

Figure 6:
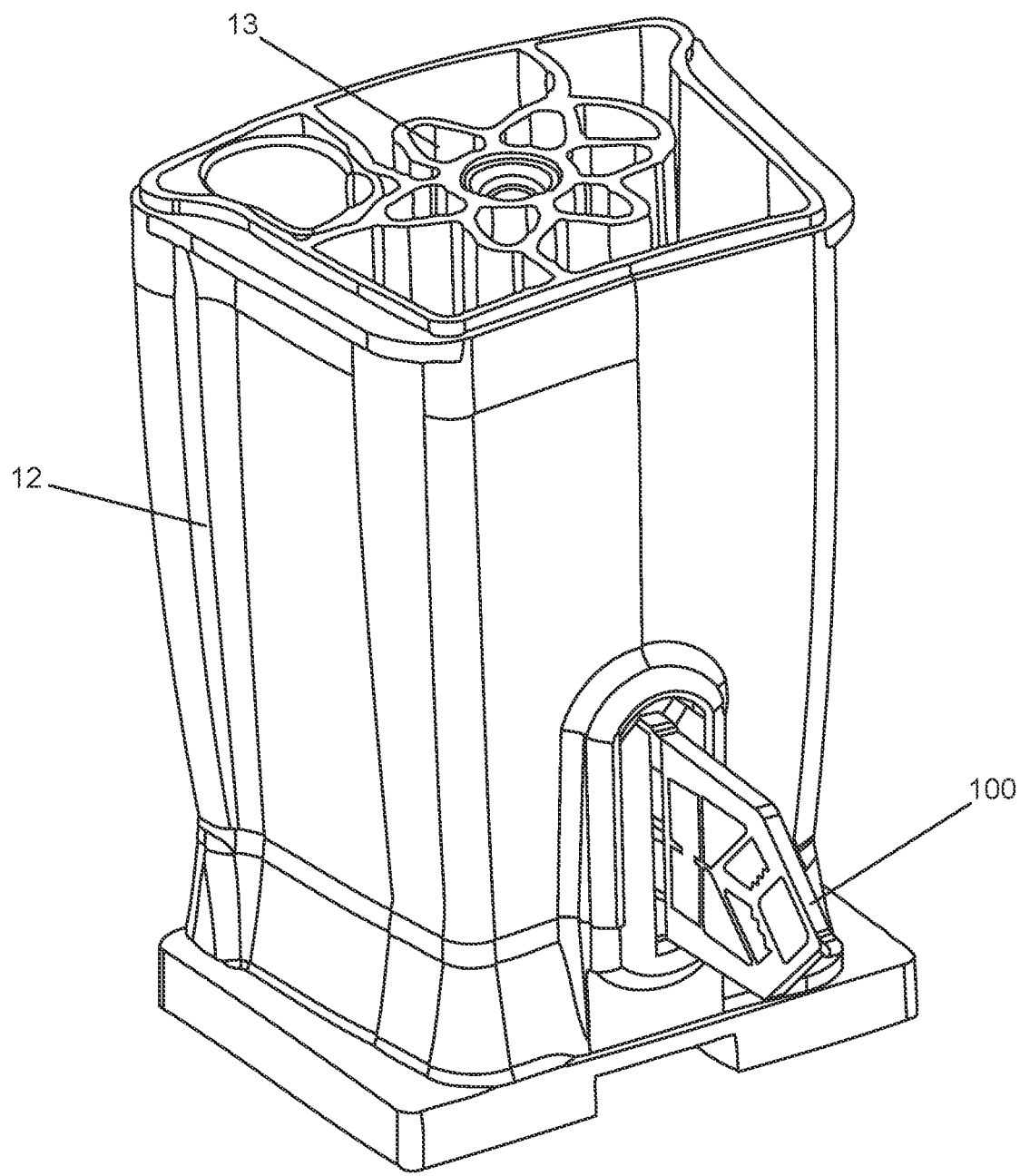
FIG. 6 shows a fluid control and processing system for providing a sample fluid to a honeycomb tube, according to some embodiments of the invention.

FIG. 6 shows a fluid control and processing cartridge 10 including a housing 12 having a plurality of chambers 13. An internally located fluid control device (not shown) and the honeycomb tube 100 are connected to different portions of the housing 12. The cartridge 10 provides the honeycomb tube with sample fluid and other fluids as necessary, by fluidically coupling with the fluidic interface 108. Typically, the cartridge comprising the honeycomb tube is used in a GeneXpert® system by Cepheid® of Sunnyvale, California, U.S.A. In some embodiments, the cartridge comprising a honeycomb tube is used in one or more modules of a heterogenous system as disclosed in U.S. Pat. App. Ser. No. 61/639,820 incorporated by reference and attached hereto as part of Appendix A. Additional details of the system 10 and methods for use are described in U.S. Pat. Nos. 8,048,386, 8,187,557, 8,119,352, and U.S. Pub. No. 2008-0038737, each of which is incorporated by reference herein, and attached hereto as Appendix A.

VI. Examples

The examples are provided by way of illustration only and not by way of limitation. Those of skill in the art will readily recognize a variety of non-critical parameters that could be changed or modified to yield essentially the same or similar results.

Example 1: Analysis of K-Ras SNP at Codons 12 and 13

An 8-probe, 8-replicate, 4-patch format was set up in this single nucleotide polymorphism analysis using a GeneXpert cartridge reaction tube. Specifically, the entire probe arrangement consisted of 4 patches of 8×8 predetermined spots on the surface of a solid substrate, which was the thin film enclosing one side of the frame of the reaction tube. In each patch, each of the 8 oligonucleotide probes of distinct nucleotide sequences was deposited (256 spots total in the tube, 100 um in diameter per spot, spot density is 50 uM and spot volume is 0.5 nL) and immobilized to a cluster of 8 pre-selected spots, resulting in 8 replicate spots for each distinct probe.

Figure 7:
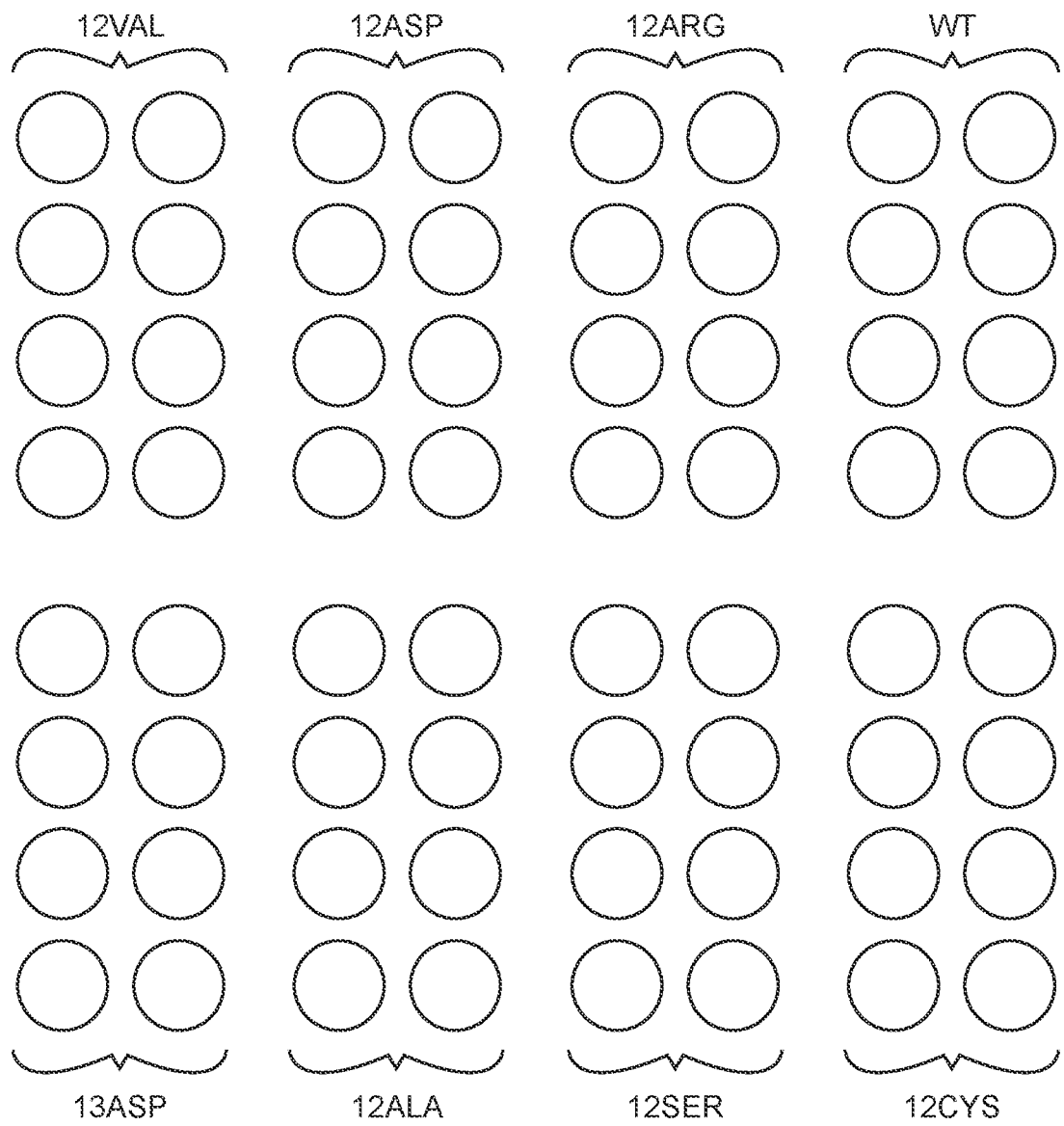
FIGS. 7-13 show steps of an example for performing multiplex PCR SNP analysis according to Example 1.

Each of the 8 oligonucleotide probes was designed in its nucleotide sequence such that it would hybridize with one version of the K-Ras sequence only. In this particular study, 1 probe was designed to hybridize with the wild-type (WT) K-Ras sequence surrounding codons 12 and 13; 1 probe to hybridize with the 12Val mutant; 1 probe to hybridize with the 12Asp mutant; 1 probe to hybridize with the 12Arg mutant; 1 probe to hybridize with the 12Cys mutant; 1 probe to hybridize with the 12Ser mutant; 1 probe to hybridize with the 12Ala mutant; and 1 probe to hybridize with the 13Asp mutant. The 8-probe arrangement on the substrate surface is shown in FIG. 7, and the probe sequences are provided in Table 1. Table 2 provides the melting temperatures of the probes.

To immobilize the probes onto the substrate surface, the surface was first cleaned up by a hydroxylation process, such that the surface energy is no less than 38 dynes/cm at about 60° contact angle and that the surface reactivity and wettability was improved for subsequent functionalization.

The functionalization process involved introducing a glycidal (epoxy) group to the substrate surface using glycidoxypropyltrimethoxysilane as a precursor. During the spotting process a covalent bond was established between the functional group and the oligonucleotide probe at its 3' end.

After functionalization of the thin film substrate and spotting of the probe, the reaction tube containing the spotted probe array was sealed by placing a second thin film on the opposite side of the frame from that of the functionalized solid substrate. The sealed reaction tube containing the 8-probe format as shown in FIG. 7 was then filled with a fluid sample, completely submerging all spots on the substrate surface. The codon 12/13 SNP analysis of the K-Ras sequence present in the sample started with an asymmetric TaqMan amplification reaction, which involved a CF4-labeled forward primer and an unlabeled reverse primer, which would hybridize with the K-Ras sequence to span the SNP region. Also included in the reaction mixture were (1) a TaqMan probe labeled with CF5 and comprising

TABLE 1

KRAS Probe Sequence

| Oligo Name | Oligo Sequence* (5'→3') | 3'-Mod |
|---|---|---|
| KRAS WT ArryPrb1 | CGCCACCAGCTCCAAC(S18)(S18)(S18)(S18) | Amino |
| KRAS 12ARG ArryPrb1 | CGCCACGAGCTCCAAC(S18)(S18)(S18)(S18) | Amino |
| KRAS 12ASP ArryPrb1 | CGCCATCAGCTCCAACT(S18)(S18)(S18)(S18) | Amino |
| KRAS 12VAL ArryPrb1 | CGCCAACAGCTCCAACT(S18)(S18)(S18)(S18) | Amino |
| KRAS 12CYS ArryPrb1 | CGCCACAAGCTCCAACT(S18)(S18)(S18)(S18) | Amino |
| KRAS 12SER ArryPrb1 | CGCCACTAGCTCCAACT(S18)(S18)(S18)(S18) | Amino |
| KRAS 12ALA ArryPrb1 | CGCCAGCAGCTCCAAC (S18)(S18)(S18)(S18) | Amino |
| KRAS 13ASP ArryPrb1 | CGTCACCAGCTCCAACT(S18)(S18)(S18)(S18) | Amino |

TABLE 2

KRAS Probes Tm (VisualOmp)

| | Probe Sequence | | | | | | | |
|---|---|---|---|---|---|---|---|---|
| | WT | 12ASP | 12VAL | 12CYS | 12SER | 12ALA | 12ARG | 13ASP |
| WT | 62.2 | 57.9 | 58.9 | 55.8 | 57.0 | 58.1 | 54.3 | 57.2 |
| 12ASP | 52.9 | 61.3 | 55.4 | 48.1 | 49.0 | 56.5 | 44.9 | 46.0 |
| 12VAL | 52.1 | 54.0 | 61.5 | 47.5 | 48.9 | 55.2 | 44.2 | 45.5 |
| 12CYS | 51.8 | 49.0 | 47.5 | 61.5 | 55.3 | 44.6 | 55.3 | 45.7 |
| 12SER | 51.3 | 48.4 | 47.6 | 55.0 | 60.4 | 44.8 | 53.7 | 45.0 |
| 12ALA | 50.3 | 54.3 | 54.3 | 47.3 | 47.2 | 62.8 | 43.9 | 42.2 |
| 12ARG | 51.3 | 49.0 | 47.3 | 53.2 | 53.8 | 44.5 | 62.4 | 44.9 |
| 13ASP | 50.8 | 44.6 | 46.2 | 42.6 | 44.3 | 45.1 | 40.3 | 60.4 | a sequence corresponding to a segment of the K-Ras sequence between the forward and reverse primers for the purpose of indicating progress of PCR; and (2) an unlabeled BlockMelt probe for the purpose of suppressing WT amplicons.

In this particular study, heating/cooling was provided on one side of the reaction chamber for the PCR process and the subsequent hybridization process. Forward primer (5'CF4) was used at the concentration of 1000 nM. Reverse primer was used at the concentration of 100 nM. TaqMan probe (5'CF5) was used at the concentration of 50 nM. The ±K-Ras WT blocker probe, unlabeled, was used at the concentration of 100 nM. After a 60-cycle PCR, temperature of the reaction chamber was set at approximately 54° C. for probe-amplicon hybridization for 1-2 hours in PCR elution buffer (Tris buffer pH 8). The reaction chamber was then washed at least once and up to 5 times with washing buffer (Tube Wash ArrayIt "Wash Buffer 2") to remove non-specific residual CF4 signal.

Figure 8:
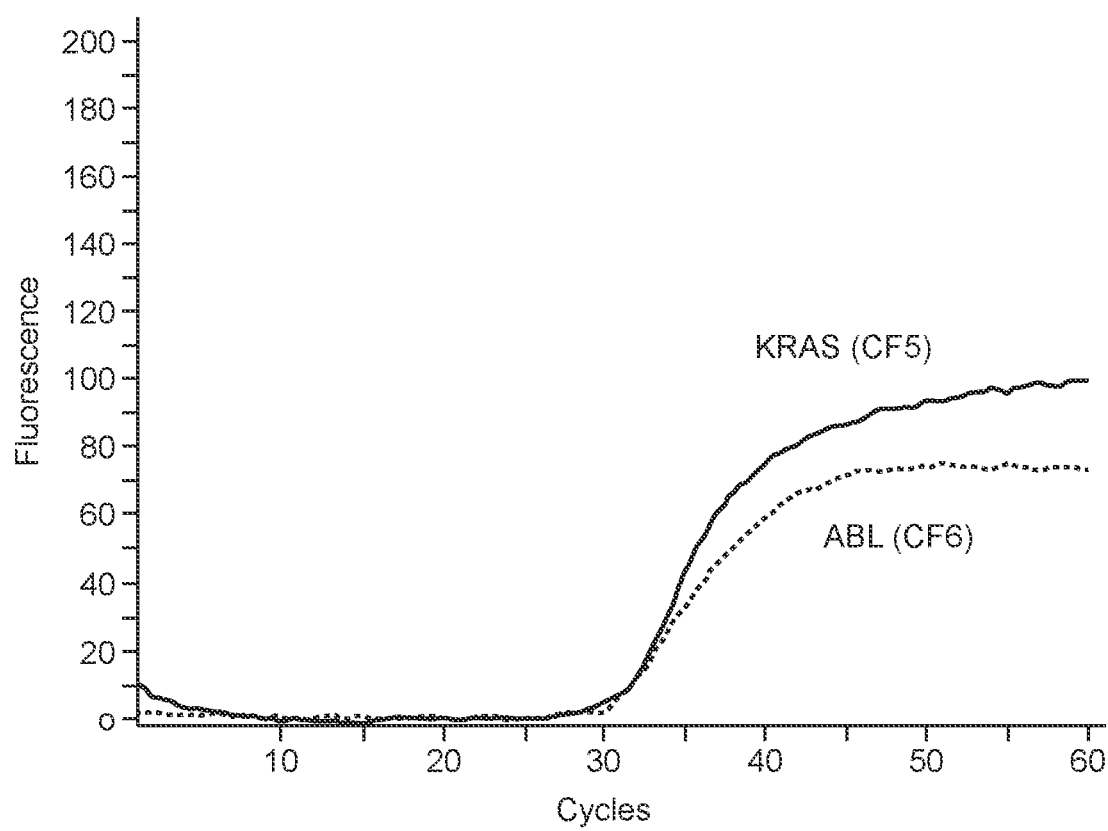
Figure 9A:
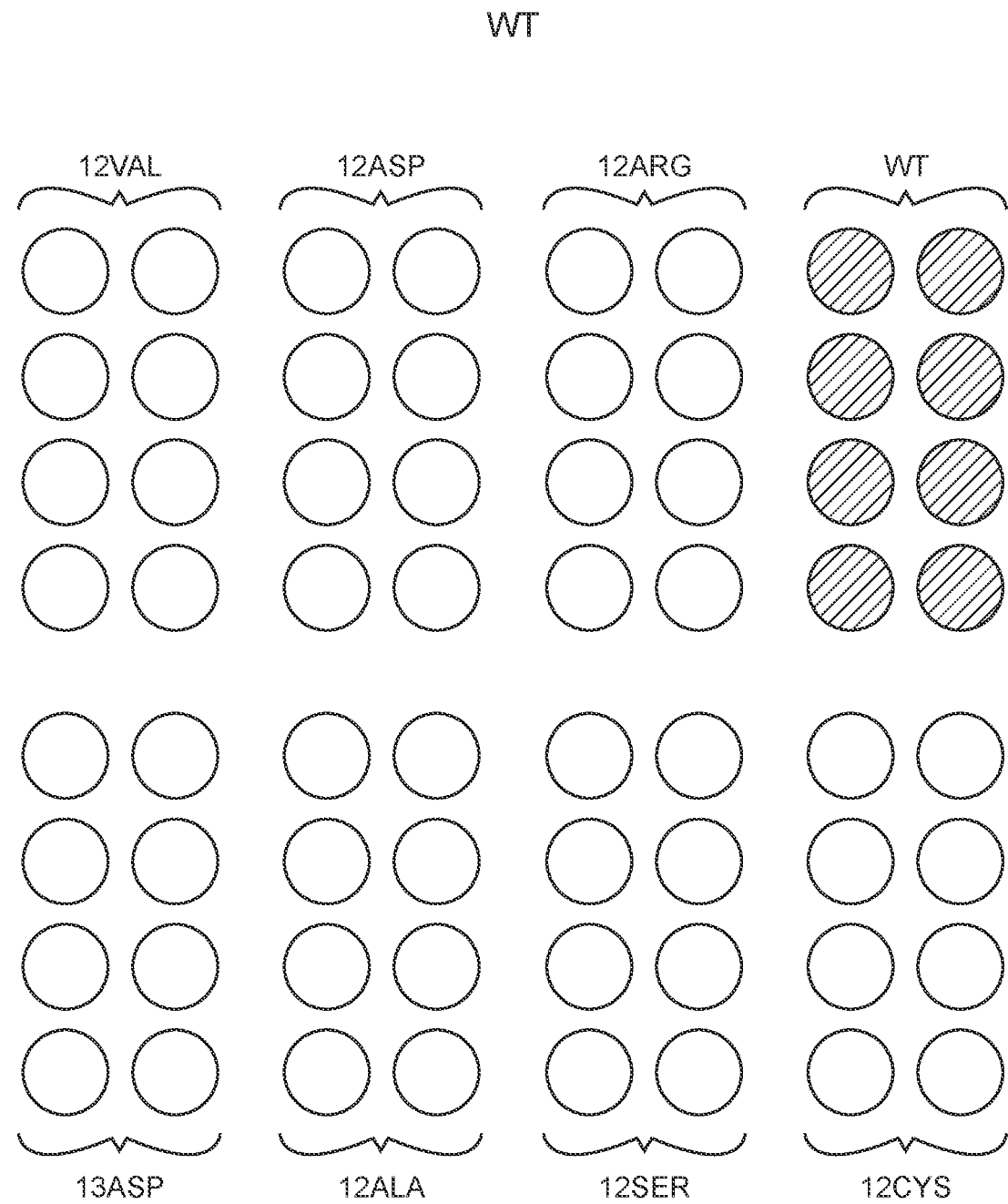
Figure 9B:
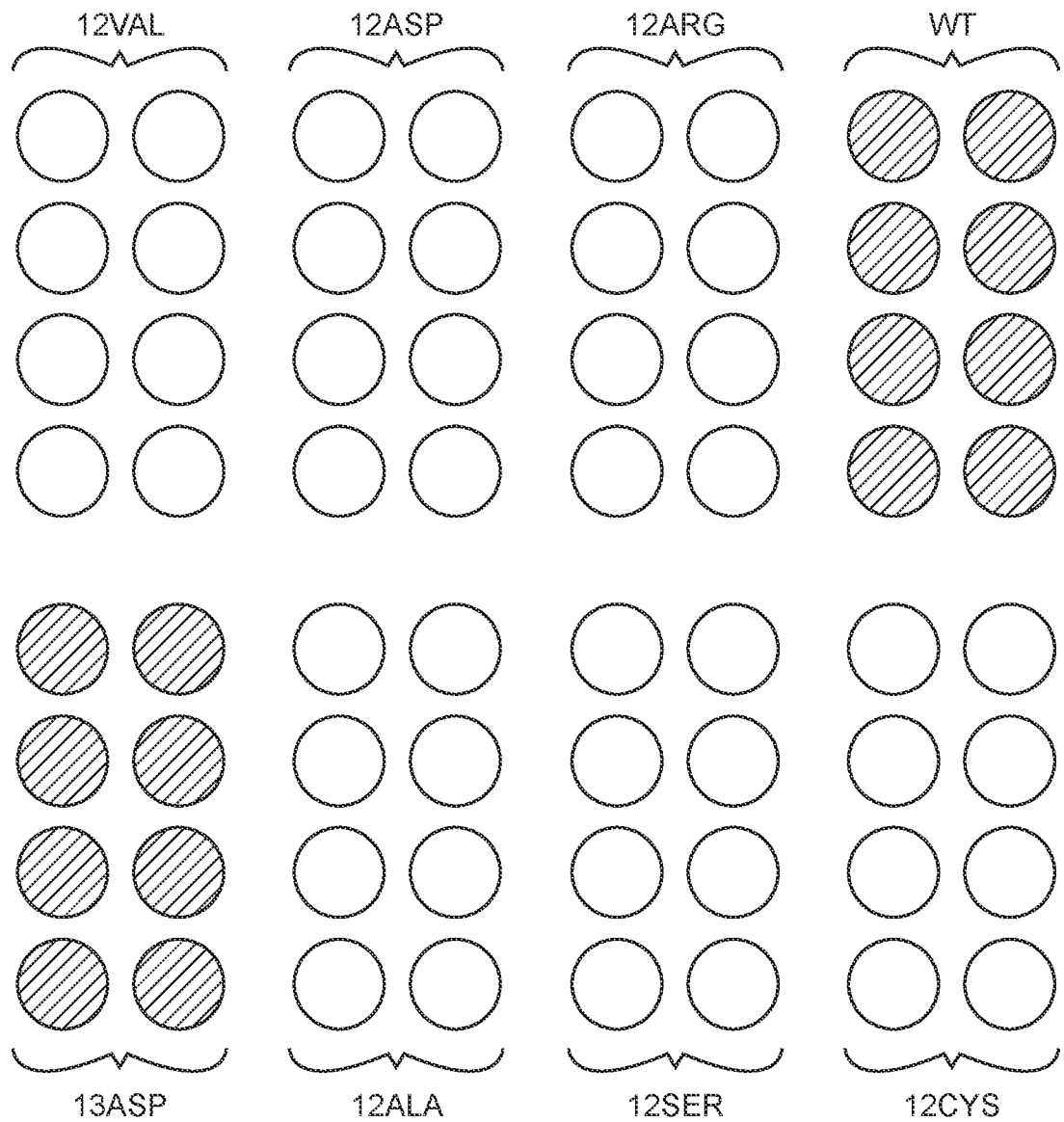
Figure 9C:
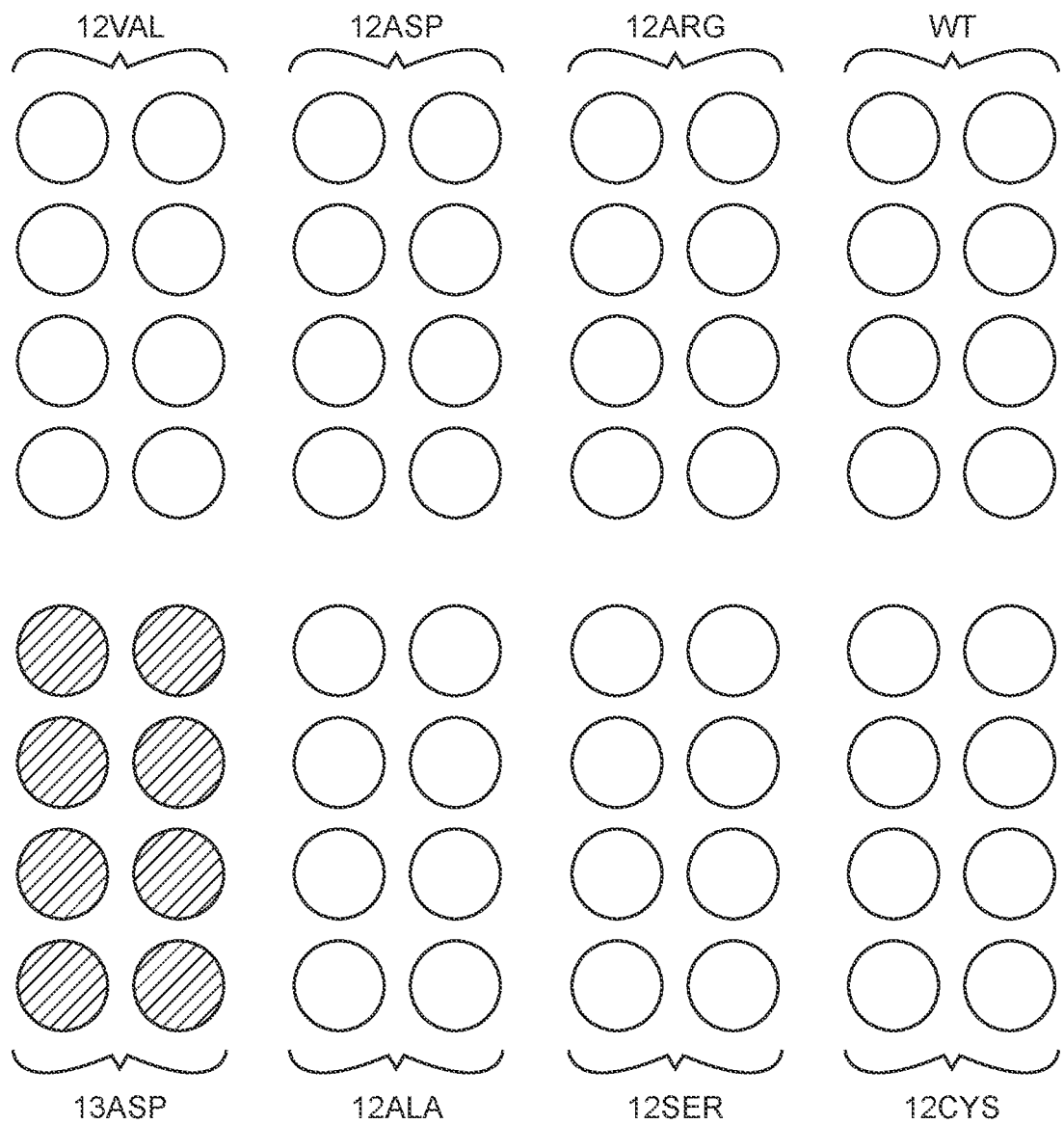
Figure 10A:
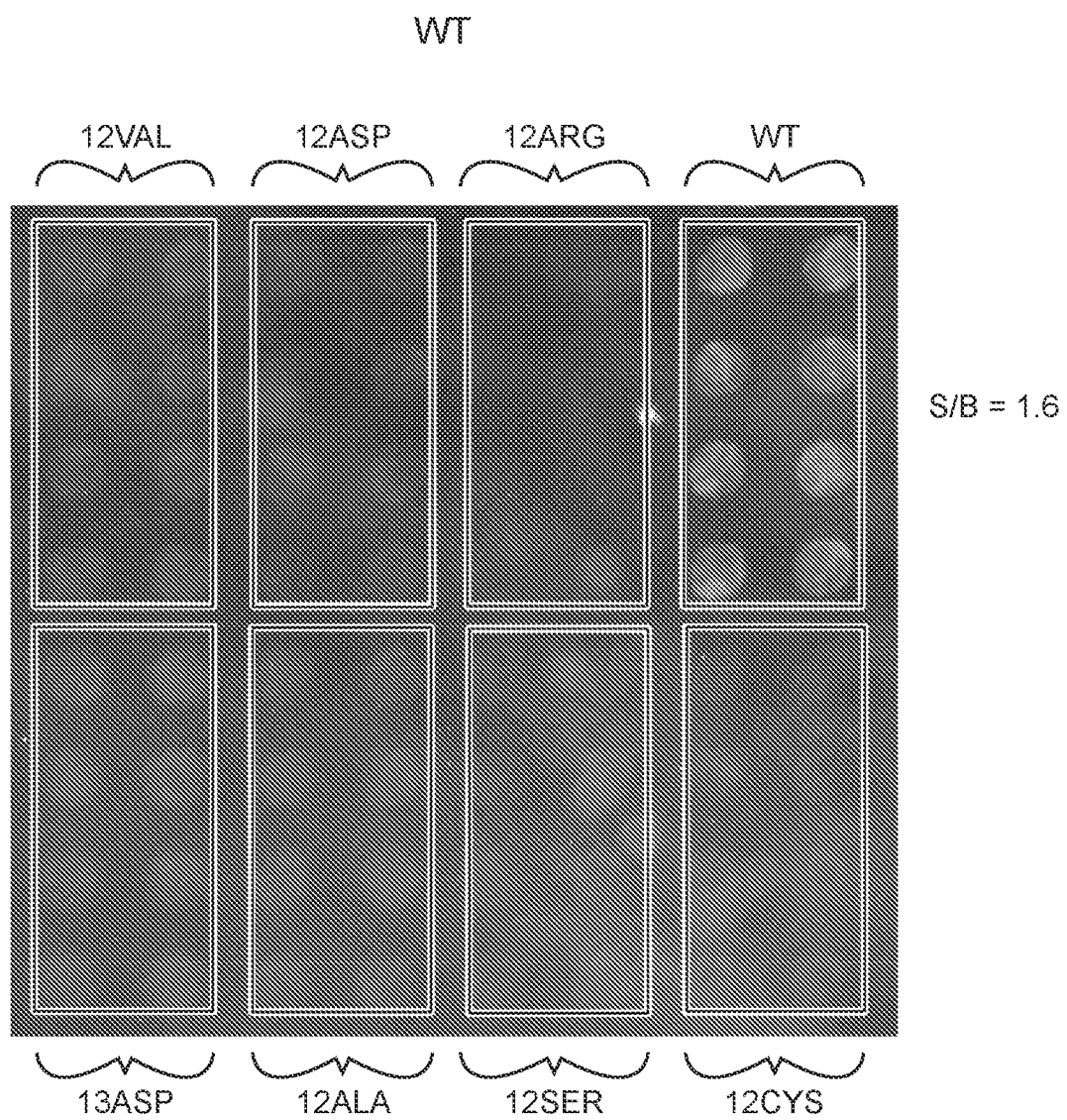
Figure 10B:
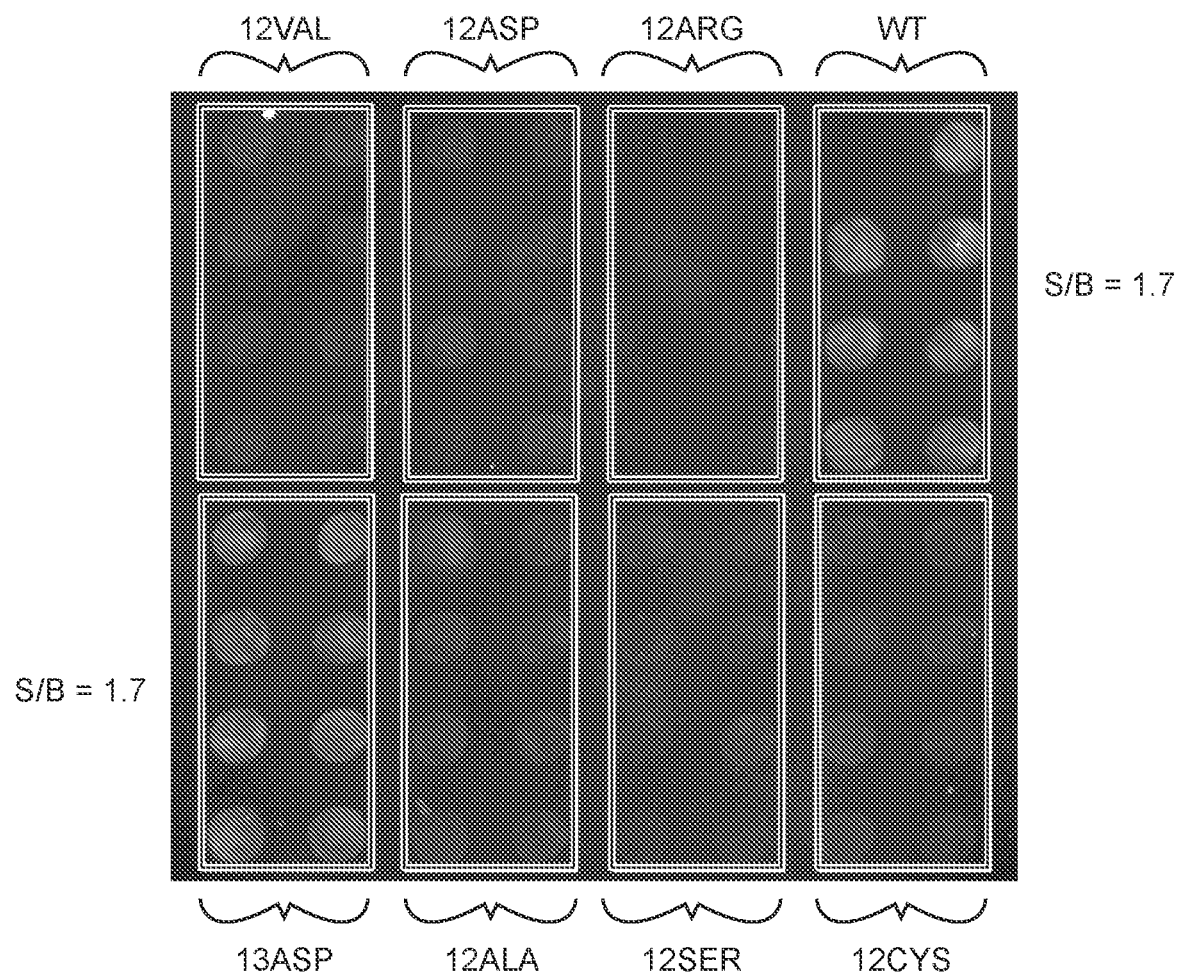
Figure 10C:
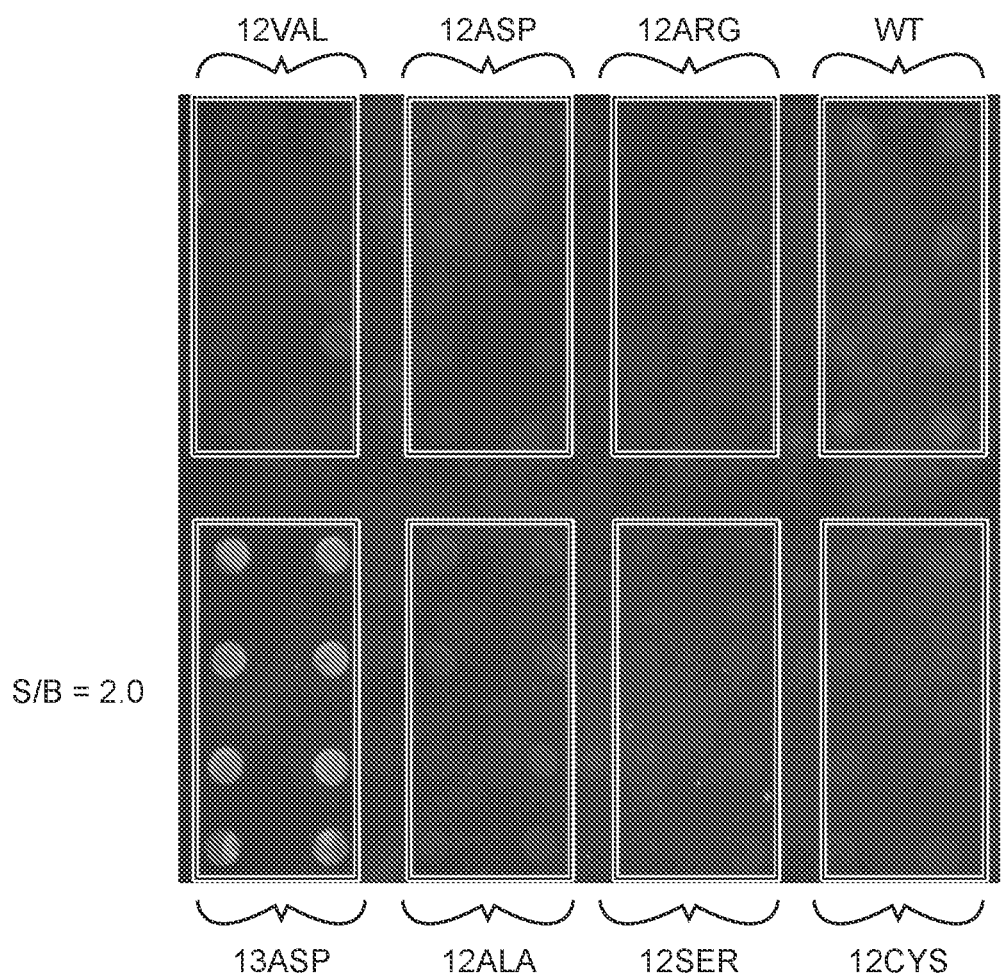
Figure 11:
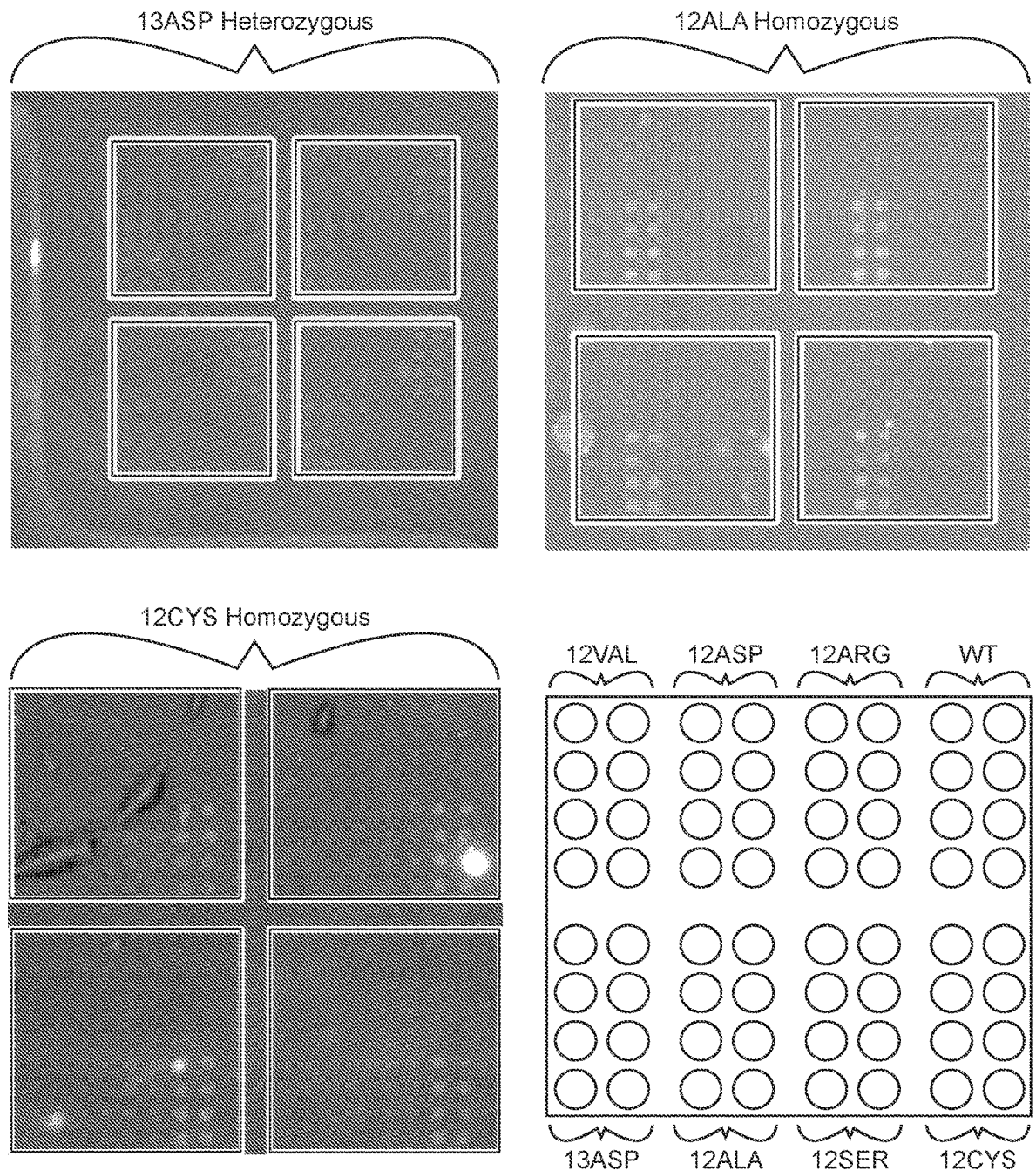
Figure 12:
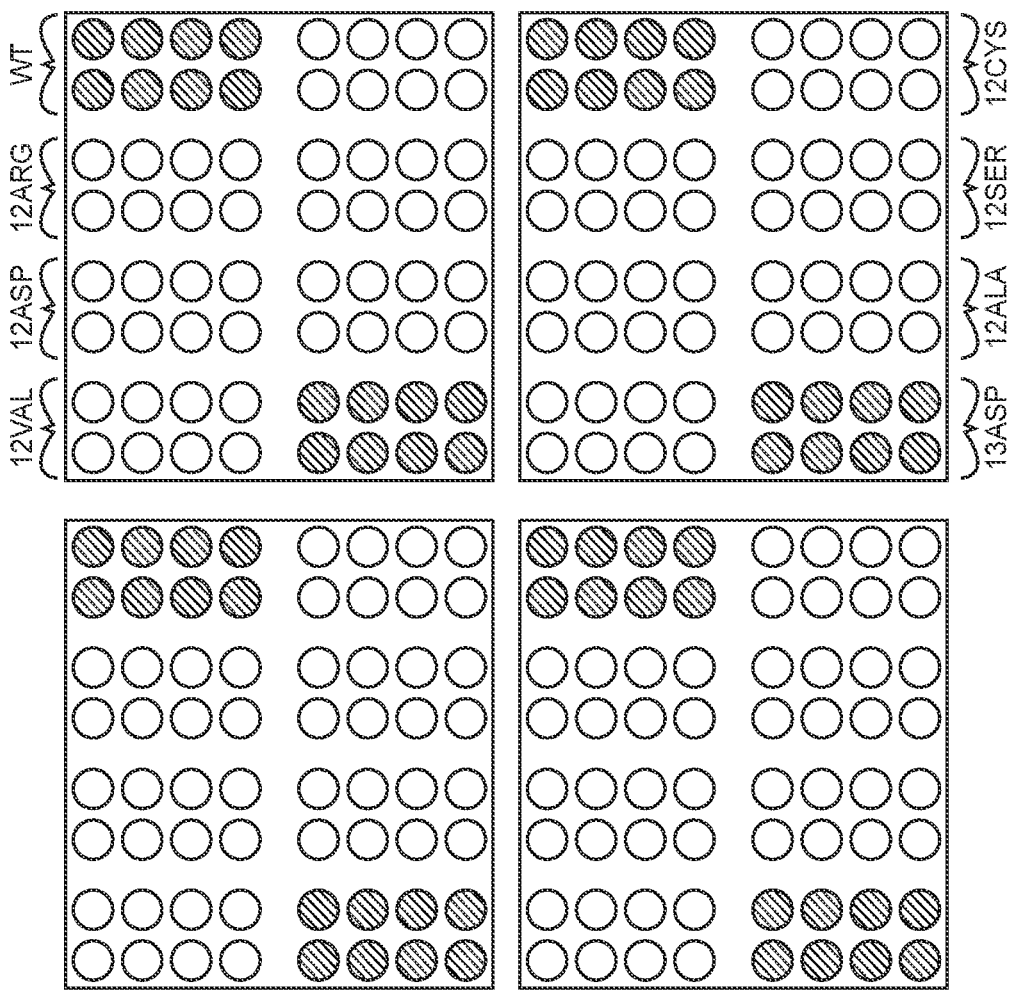
Figure 12:
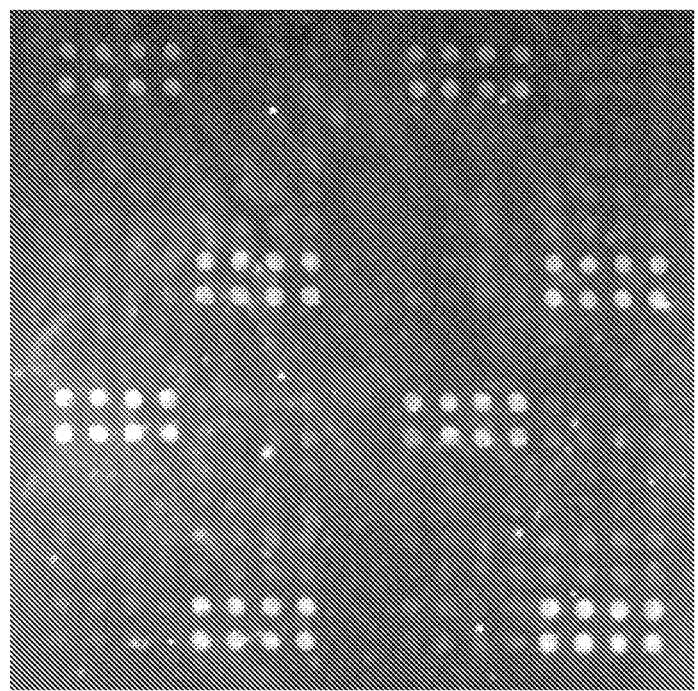
Figure 13:
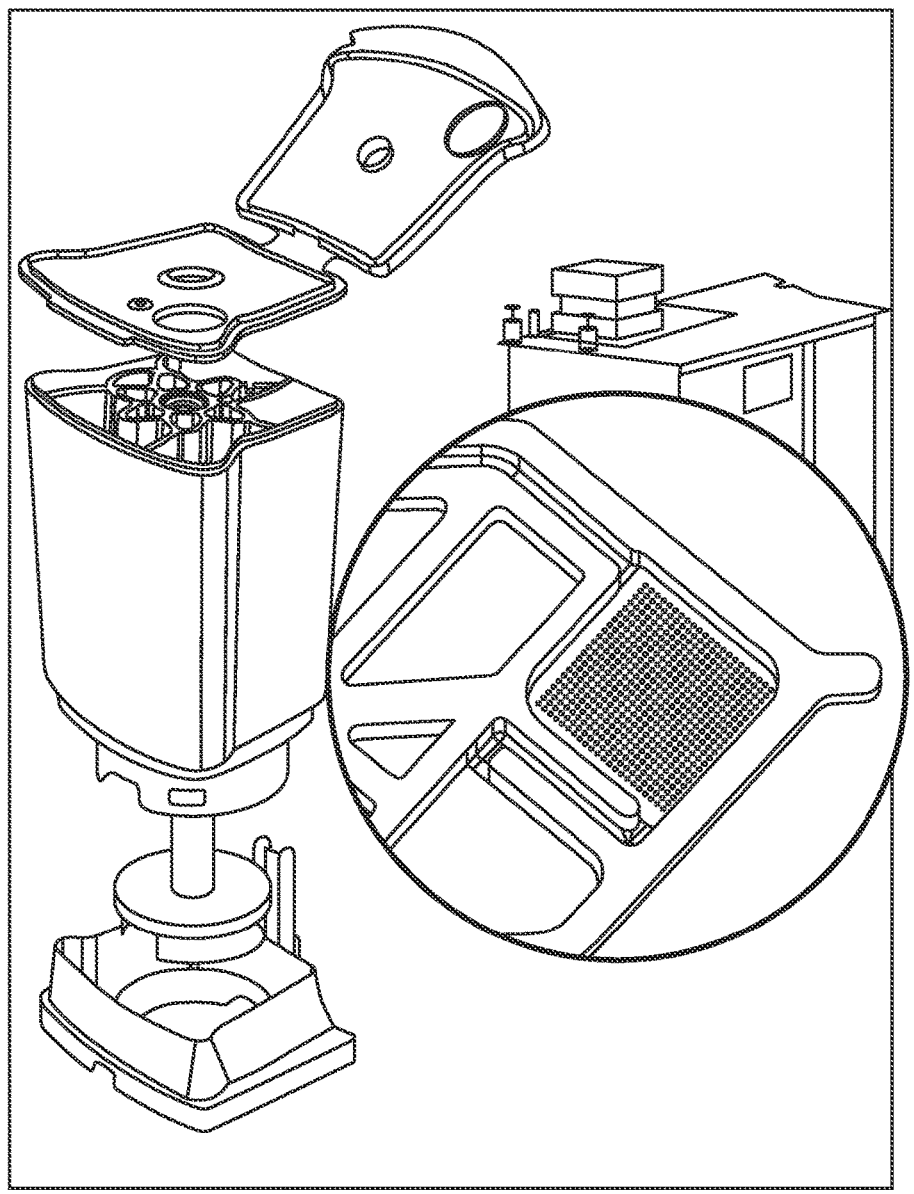

Three different samples were analyzed: the K-Ras WT cell line (homozygous normal), the K-Ras CCL cells (heterozygous), and the K-Ras CCL cells, blocked (homozygous mutant). FIG. 8 shows the fluorescent signal curve during the 60-cycle PCR. FIGS. 9A-C show projected results from the WT, heterozygous 13Asp mutant, and homozygous 13Asp mutant cell samples. FIGS. 10A-C show actual results from the samples. A global view of the entire probe spotting pattern is shown in FIG. 11. FIG. 12 shows a global view of the entire probe spotting pattern as seen under an integrated microscope following excitation.

Example 2: Reagent Loading into Dry Wells

The honeycomb tube 100 used in this study was created by injection molding. The part is molded with one supporting well-substrate 120 in the PCR area. Nanowells were created by the excimer laser drilling at 193 nm. The dimension of the nanowells used in this study is 150 vim in diameter and around 150 vim in depth with pitch distance is at 250 µm. These wells are blind holes and can hold up to 2.6 nL.

As shown in FIG. 3A, green food dye was then printed by using NanoPrint® by ArrayIt® with the micro spotting pin (model number #946MP3 with 100 µm in diameter at the tip of the pin). Each drop from the pin has a volume of 0.7 nL. NanoPrint® is a commercialized microarray printer by ArrayIt®, and is programmable for different pitch distance and can deliver the quantity of liquid at multiplex of 0.7 nL when using 946MP3. There is selection of pins to choose. The smallest micro spotting pin can deliver only 0.35 nL per drop. In actual case, the green food dye would be the primer set or primer set with enzyme for PCR process. Each individual nanowell can have different primer set for particular nucleic acid target to be amplified during PCR process. After spotting, a freeze dry or lyophilization process could happen for storage purpose.

Example 3: Discontinuous Dewetting for Sample Filling and Sealing

The honeycomb tube 100 is used in this example (and example 4) was constructed from polypropylene. The honeycomb tube 100 is molded with one supporting well-substrate 120 in the PCR area. A plurality of nanowells were created using excimer Laser at 193 nm wavelength. The dimension of the nanowells used in this example is 150 µm in diameter and around 250 µm in depth with pitch distance is at 250 µm. These wells are through holes and can hold up to 4.4 nanoliter. The honeycomb tube 100 was then sealed by the polypropylene film at both sides of the tube. Each individual well was not sealed but the whole diamond area (25 µL area) for PCR was sealed. The honeycomb tube 100 was coupled to the cartridge 10 shown in FIG. 6.

A PCR buffer (50 mM Tris, PH8.6) first mixed with surfactant (0.1% Tween) to enhance the wetting on the polypropylene surface because the hydrophobity of polypropylene. A small quantity of yellow food dye was dropped in the PCR buffer to enhance the visualization. This PCR buffer was then added into one of the chambers 13 in the cartridge 10 shown in FIG. 6. Mineral oil (CAS #8042-47-5) was added into another chamber. A commercially available GeneXpert® system by Cepheid® was used to control the cartridge 10 to drive liquid filling of the honeycomb tube 100.

The GeneXpert® system was programmed to deliver the PCR buffer through the fluid channel into the well chamber 118 at a rate of 1 µL/sec. PCR buffer filled each nanowell in the well chamber 118 and some excessive PCR buffer exited via the top fluid channel. After the PCR chamber of the honeycomb tube 100 was filled, PCR buffer in the tube 100 was then drained at a rate of 5 uL/sec from the bottom of the well chamber and into the fluid channel. The buffer was pulled from the top fluid channel back into the inlet passage 128 (bottom-most fluid channel). After draining, PCR buffer remained in each individual nanowell, via capillary forces. Despite the draining procedure, PCR buffer in each nanowell did not escape out. After the PCR buffer was completely drained via the inlet passage 128, mineral oil was introduced into the well-chamber 118 at 1 µL/sec. The gap between the sealing film and the polypropylene substrate with nanowells was filled by the mineral oil, as shown in FIG. 4E.

Example 4: Continuous Wetting for Sample Filling and Sealing

Using the same honeycomb tube 100 as in Example 3, the nanowells were filled with PCR buffer using the discontinuous dewetting method discussed in Example 3. However, after individual nanowell was filled by the PCR buffer, mineral oil was introduced into the well-chamber 118 of the honeycomb tube to continue filling the PCR chamber at 5 µL/sec from the inlet passage 128 (instead of draining the PCR buffer as in Example 3). Mineral oil displaced the PCR buffer in the well-chamber 118 (i.e. between the polypropylene substrate and the top sealing film) on top of the nanowell. This method is referred to as "continuous wetting" because two liquids continuously wet the surface. The first liquid (PCR buffer) wets the surface and fills the nanowells. The second liquid (mineral oil) continuously wets the surface, but does not fill "in" each nanowell—because the surface tension and capillary force keeps the first aqueous liquid in the nanowell.

Both methods used in Examples 3 and 4 successfully introduced the desired PCR buffer into the nanowell and used mineral oil to isolate PCR buffer in each individual nanowell. The mineral oil cap has a further advantage that it can prevent the aqueous liquid in the nanowell from evaporating during the thermal cycling process.

All patents, patent applications, and other publications, including GenBank Accession Numbers, cited in this application are incorporated by reference in the entirety for all purposes.

What is claimed is:

1. A method of depositing a liquid sample in wells of a well array in a well chamber of a reaction vessel comprising a planar frame elongated length-wise between opposite ends and having a fluidic interface at one end of the opposite ends, the fluidic interface having a fluidic inlet and a fluidic outlet, the planar frame extending length-wise along a length thereof, the length being longer than a width of the planar frame, and the reaction vessel having a fluidic path extending between the fluidic inlet and the fluidic outlet, the well chamber being disposed along the fluidic path and having a plurality of wells defining the well array, the method comprising:

introducing the liquid sample, by pressurized fluid flow, through the fluidic inlet of the fluidic interface of the reaction vessel and advancing the liquid sample along the fluidic path;

filling the well chamber along the fluidic path with the liquid sample by further advancing the liquid sample along the fluidic path thereby depositing the liquid sample within the plurality of wells of the well chamber; and evacuating at least a portion of the liquid sample from the well chamber outside of the plurality of wells via application of pressure to the fluidic interface such that at least some of the liquid sample remains deposited within the plurality of wells of the well array.

2. The method of claim 1 wherein the planar frame is positioned such that a major plane along which the planar frame extends is oriented vertically during filling of the well chamber.

3. The method of claim 1 wherein the fluidic path and well chamber are configured such that when the planar frame is oriented vertically during filling, an entrance of the well array is disposed along a bottom of the well chamber and an exit of the well chamber is disposed along a top of the well chamber so as to provide controlled fluid flow into the plurality wells upon filling of the well chamber through the entrance of the well chamber.

4. The method of claim 1, wherein the plurality of wells includes between 100 and 1,500 wells.

5. The method of claim 1, wherein the plurality of wells each have a diameter within a range from 50 to 500 um.

6. The method of claim 1, wherein the plurality of wells comprises a plurality of nanowells each having a depth from 25 μm to 1000 μm.

7. The method of claim 1, wherein the fluidic interface is configured to be coupled to a liquid sample cartridge so as to fluidically couple the fluidic inlet and the fluidic outlet with corresponding fluid ports of the liquid sample cartridge.

8. The method of claim 1, further comprising:

filling the well chamber with a hydrophobic fluid substance after the evacuating the at least a portion of the liquid sample from the well chamber outside of the plurality of wells.

9. The method of claim 8, wherein the hydrophobic fluid substance is an oil and is supplied from an oil chamber of the planar frame that is fluidically connected with the well chamber.

10. The method of claim 1, wherein the fluidic path includes a serpentine channel portion between the fluidic inlet and the well chamber, the serpentine channel including at least two elongate channel portions connected in a serpentine manner.

11. The method of claim 1, wherein the reaction vessel comprises a first planar substrate and a second planar substrate, the fluidic path disposed between the first planar substrate and the second planar substrate, the method further comprising:

applying heating and cooling cycles to the first planar substrate and the second planar substrate.

12. The method of claim 1, wherein application of pressure comprises applying a positive or negative pressure via the fluidic inlet or the fluidic outlet of the fluidic interface.

13. The method of claim 1, wherein the well chamber is disposed along the opposite end as the one end of the reaction tube having the fluidic interface.

14. A method of filling a plurality of wells in a well chamber of a reaction vessel comprising a body elongated between opposite ends and having a fluidic interface at one end of the opposite ends, the fluidic interface having a fluidic inlet and a fluidic outlet, and the reaction vessel having a fluidic path extending length-wise between the fluidic inlet and the fluidic outlet, the body extending length-wise along a length thereof, the length being greater than a width of the body, the well chamber being disposed along the fluidic path and having a plurality of wells defining the well array, the method comprising:
  introducing a liquid sample, by pressurized fluid flow, through the fluidic inlet of the fluidic interface of the reaction vessel and advancing the liquid sample along the fluidic path;
  filling the well chamber along the fluidic path with the liquid sample by further advancing the liquid sample along the fluidic path thereby depositing the liquid sample within the plurality of wells of the well chamber; and
  evacuating at least a portion of the liquid sample from the well chamber outside of the plurality of wells via application of pressure to the fluidic interface such that at least some of the liquid sample remains deposited within the plurality of wells of the well array.

15. The method of claim 14 wherein the body is planar having a major plane that is oriented vertically during filling of the well chamber.

16. The method of claim 15 wherein the fluidic path and well chamber are configured such that when the body is oriented vertically during filling, an entrance of the well array is disposed along a bottom of the well chamber and an exit of the well chamber is disposed along a top of the well chamber so as to provide controlled fluid flow into the plurality of wells upon filling of the well chamber through the entrance of the well chamber.

17. The method of claim 14, wherein the plurality of wells includes between 100 and 1,500 wells.

18. The method of claim 14, wherein the plurality of wells each have a diameter within a range from 50 to 500 μm.

19. The method of claim 14, wherein the plurality of wells comprises a plurality of nanowells each having a depth from 25 μm to 1000 μm.

20. The method of claim 14, wherein the fluidic interface is configured to be coupled to a liquid sample cartridge so as to fluidically couple the fluidic inlet and the fluidic outlet with corresponding fluid ports of the liquid sample cartridge.

21. The method of claim 14, further comprising:
  filling the well chamber with a hydrophobic fluid substance after the evacuating the at least a portion of the liquid sample from the well chamber outside of the plurality of wells.

22. The method of claim 21, wherein the hydrophobic fluid substance is an oil and is supplied from an oil chamber of the planar frame that is fluidically connected with the well chamber.

23. The method of claim 14, wherein the fluidic path includes a serpentine channel portion between the fluidic inlet and the well chamber, the serpentine channel including at least two elongate channel portions connected in a serpentine manner.

24. The method of claim 14, wherein application of pressure comprises applying a positive or negative pressure via the fluidic inlet or the fluidic outlet of the fluidic interface.

25. The method of claim 14, wherein the well chamber is disposed along the opposite end of the reaction tube having the fluidic interface.

* * * * *

SEQUENCE LISTING

```
Sequence total quantity: 8
SEQ ID NO: 1                moltype = DNA  length = 16
FEATURE                     Location/Qualifiers
misc_feature                1..16
                            note = synthetic oligonucleotide probe KRAS WT ArryPrb1 for
                             wild-type (WT) K-Ras sequence surrounding codons 12 and 13
modified_base               16
                            mod_base = OTHER
                            note = c modified by 3' amino group
source                      1..16
                            mol_type = other DNA
                            organism = synthetic construct
SEQUENCE: 1
cgccaccagc tccaac                                                             16

SEQ ID NO: 2                moltype = DNA  length = 16
FEATURE                     Location/Qualifiers
misc_feature                1..16
                            note = synthetic oligonucleotide probe KRAS 12ARG ArryPrb1
                             for 12Arg mutant K-Ras sequence
modified_base               16
                            mod_base = OTHER
                            note = c modified by 3' amino group
source                      1..16
                            mol_type = other DNA
                            organism = synthetic construct
SEQUENCE: 2
cgccacgagc tccaac                                                             16

SEQ ID NO: 3                moltype = DNA  length = 17
FEATURE                     Location/Qualifiers
misc_feature                1..17
                            note = synthetic oligonucleotide probe KRAS 12ASP ArryPrb1
                             for 12Asp mutant K-Ras sequence
modified_base               17
                            mod_base = OTHER
                            note = t modified by 3' amino group
source                      1..17
                            mol_type = other DNA
                            organism = synthetic construct
SEQUENCE: 3
cgccatcagc tccaact                                                            17

SEQ ID NO: 4                moltype = DNA  length = 17
FEATURE                     Location/Qualifiers
misc_feature                1..17
                            note = synthetic oligonucleotide probe KRAS 12VAL ArryPrb1
                             for 12Val mutant K-Ras sequence
modified_base               17
                            mod_base = OTHER
                            note = t modified by 3' amino group
source                      1..17
                            mol_type = other DNA
                            organism = synthetic construct
SEQUENCE: 4
cgccaacagc tccaact                                                            17

SEQ ID NO: 5                moltype = DNA  length = 17
FEATURE                     Location/Qualifiers
misc_feature                1..17
                            note = synthetic oligonucleotide probe KRAS 12CYS ArryPrb1
                             for 12Cys mutation K-Ras sequence
modified_base               17
                            mod_base = OTHER
                            note = t modified by 3' amino group
source                      1..17
                            mol_type = other DNA
                            organism = synthetic construct
SEQUENCE: 5
cgccacaagc tccaact                                                            17

SEQ ID NO: 6                moltype = DNA  length = 17
FEATURE                     Location/Qualifiers
misc_feature                1..17
                            note = synthetic oligonucleotide probe KRAS 12SER ArryPrb1
                             for 12Ser mutant K-Ras sequence
modified_base               17
                            mod_base = OTHER
```

```
                            note = t modified by 3' amino group
source                      1..17
                            mol_type = other DNA
                            organism = synthetic construct
SEQUENCE: 6
cgccactagc tccaact                                                        17

SEQ ID NO: 7                moltype = DNA  length = 16
FEATURE                     Location/Qualifiers
misc_feature                1..16
                            note = synthetic oligonucleotide probe KRAS 12ALA ArryPrb1
                             for 12Ala mutant K-Ras sequence
modified_base               16
                            mod_base = OTHER
                            note = c modified by 3' amino group
source                      1..16
                            mol_type = other DNA
                            organism = synthetic construct
SEQUENCE: 7
cgccagcagc tccaac                                                         16

SEQ ID NO: 8                moltype = DNA  length = 17
FEATURE                     Location/Qualifiers
misc_feature                1..17
                            note = synthetic oligonucleotide probe KRAS 13ASP ArryPrb1
                             for 13Asp mutant K-Ras sequence
modified_base               17
                            mod_base = OTHER
                            note = t modified by 3' amino group
source                      1..17
                            mol_type = other DNA
                            organism = synthetic construct
SEQUENCE: 8
cgtcaccagc tccaact                                                        17
```